(12) United States Patent
Nakata et al.

(10) Patent No.: US 10,301,177 B2
(45) Date of Patent: May 28, 2019

(54) HYDROGEN DESORPTION METHOD AND DEHYDROGENATION APPARATUS

(71) Applicant: Panasonic Intellectual Property Management Co., Ltd., Osaka (JP)

(72) Inventors: Yuki Nakata, Osaka (JP); Hyunjeong Nam, Nara (JP); Saifullah Badar, Osaka (JP); Manabu Kanou, Osaka (JP); Yuji Zenitani, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 76 days.

(21) Appl. No.: 15/612,074

(22) Filed: Jun. 2, 2017

(65) Prior Publication Data

US 2017/0362084 A1    Dec. 21, 2017

(30) Foreign Application Priority Data

Jun. 16, 2016 (JP) .................... 2016-120079
Jan. 24, 2017 (JP) .................... 2017-010454

(51) Int. Cl.
| | | |
|---|---|---|
| *C25B 3/00* | (2006.01) | |
| *C25B 3/04* | (2006.01) | |
| *C01B 3/00* | (2006.01) | |
| *C07C 5/367* | (2006.01) | |
| *C25B 1/02* | (2006.01) | |
| *C25B 11/04* | (2006.01) | |
| *G01N 30/02* | (2006.01) | |

(Continued)

(52) U.S. Cl.
CPC ............ *C01B 3/0015* (2013.01); *C07C 5/367* (2013.01); *C25B 1/02* (2013.01); *C25B 3/00* (2013.01); *C25B 3/04* (2013.01); *C25B 11/04* (2013.01); *C25B 13/08* (2013.01); *C25B 15/00* (2013.01); *G01N 2030/025* (2013.01); *Y02E 60/328* (2013.01)

(58) Field of Classification Search
None
See application file for complete search history.

(56) References Cited

U.S. PATENT DOCUMENTS

| | | | |
|---|---|---|---|
| 2011/0171119 A1 | 7/2011 | Yazami | |
| 2014/0318979 A1* | 10/2014 | Cronin | .................... C25B 1/003 205/340 |
| 2015/0259200 A1 | 9/2015 | Kalb | |

FOREIGN PATENT DOCUMENTS

| | | |
|---|---|---|
| JP | 2005-211845 | 8/2005 |
| JP | 2015-147998 A | 8/2015 |

OTHER PUBLICATIONS

Masaru Ichikawa, "Book for understanding hydrogen energy, hydrogen society and hydrogen business", Ohmsha Ltd., pp. 108-109, Feb. 5, 2007. (Partial Translation).

(Continued)

*Primary Examiner* — Brian W Cohen
(74) *Attorney, Agent, or Firm* — McDermott Will & Emery LLP

(57) ABSTRACT

A hydrogen desorption method includes a step of bringing a liquid containing an alicyclic saturated hydrocarbon having a tertiary carbon atom bearing a saturated hydrocarbon side chain, a quinone, and an electrolyte into contact with a anode and a step of desorbing hydrogen from the alicyclic saturated hydrocarbon having a tertiary carbon atom bearing a saturated hydrocarbon side chain.

10 Claims, 13 Drawing Sheets

(51) Int. Cl.
  *C25B 13/08* (2006.01)
  *C25B 15/00* (2006.01)

(56) References Cited

OTHER PUBLICATIONS

N. Dost et al., "The Dehydrogenation of Hydrocarbons by Means of Quinones", Recueil, 70, 403-411, 1951.
Peter F. Driscoll et al., "Electrochemical Redox Catalysis for Electrochemical Dehydrogenation of Liquid Hydrogen Carrier Fuels for Energy Storage and Conversion", Journal of The Electrochemical Society,160, G3152-G3158, May 11, 2013.
Peter F. Driscoll et al., "Redox Catalysis for Dehydrogenation of Liquid Hydrogen Carrier Fuels for Energy Storage and Conversion", ECS Transactions, 35 (28) 3-17 (2011), Oct. 11, 2011.
The Extended European Search Report dated Oct. 17, 2017 for the related European Patent Application No. 17173489.0.
The Extended European Search Report dated Oct. 18, 2017 for the related European Patent Application No. 17173923.8.
N.Dost et al: "The dehydrogenation of hydrocarbons by means of quinones: I. action of Chloranil", Recueil Des Travaux Chimiques Des Pays-Bas, vol. 70, No. 5, Jan. 1, 1951 (Jan. 1, 1951), pp. 403-411, XP055411540.
P. N. Pintauro et al: "The role of supporting electrolyte during the electrocatalytic hydrogenation of aromatic compounds", Journal of App li ed Electrochemistry., vol. 21, No. 9, Sep. 1, 1991 (Sep. 1, 1991), pp. 799-804, XP055220681.

\* cited by examiner

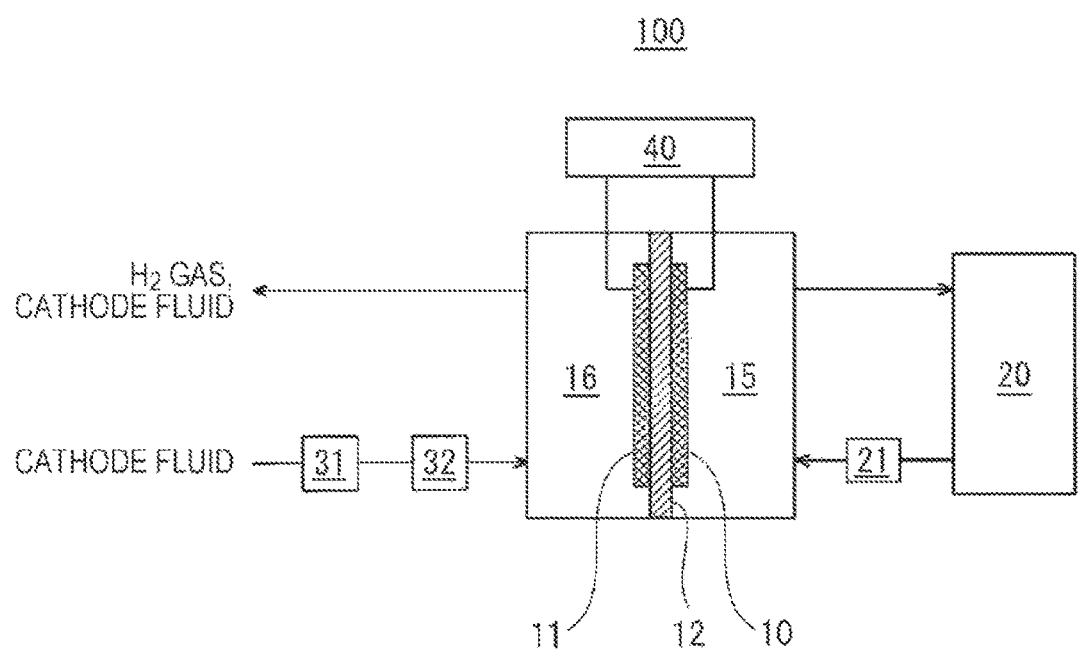

n = 1 n = 2 n = 3

HYDROGEN DESORPTION METHOD AND DEHYDROGENATION APPARATUS

BACKGROUND

1. Technical Field

The present disclosure relates to a hydrogen desorption method and a dehydrogenation apparatus.

2. Description of the Related Art

In recent years, technologies utilizing hydrogen energy have been actively studied. For example, fuel cells for domestic use and industrial use and fuel cell vehicles have been put to practical use. Unlike electric energy, in principle, hydrogen can be stored as it is. However, since hydrogen is a gas at normal temperature and pressure, in particular, the volume density of the energy is small. Accordingly, hydrogen is, for example, stored in a hydrogen cylinder under pressure, maintained in a liquid state, or occluded in a hydrogen storage alloy.

"Suiso enerugi ga wakaru hon Suiso shakai to suiso bizinesu (Easy book for understanding hydrogen energy—Hydrogen society and Hydrogen business (Ohmsha, Ltd.)" proposes an organic hydride method as a hydrogen-storing method other than the above-mentioned methods. In the organic hydride method, hydrogen is stored in a state being bound to an aromatic compound. For example, hydrogen is bound to toluene to generate methylcyclohexane, and hydrogen is stored in the state of methylcyclohexane. Methylcyclohexane returns to toluene by desorbing hydrogen. Similarly, hydrogen can be stored by utilizing exchange between naphthalene and decahydronaphthalene (decalin).

In the organic hydride method, the compound to which hydrogen is bound and the compound from which hydrogen is desorbed are liquid at normal temperature and can be treated as compounds belonging to petroleum, such as gasoline and kerosene. Since these compounds are stable and are recyclable, these compounds seem to be useful as hydrogen-storing and hydrogen-supplying means.

However, in the organic hydride method, since the hydrogen desorption reaction is an endothermic reaction, energy from the outside is necessary for the desorption of hydrogen. Accordingly, catalysts capable of desorbing hydrogen with thermal energy have been studied (Japanese Unexamined Patent Application Publication No. 2005-211845; N. Dost, K. Van Nes, Recueil, 70; 403-411 (1951)). Peter F. Driscoll, Elise Deunf, Leah Rubin, John Arnold, John B. Kerr, Journal of Electron Society, 160 G3152-G3158 (2013) proposes a method of electrochemically desorbing hydrogen.

Peter F. Driscoll et. al, ESC Transactions, 35 (28), 3-17 (2011) reports a study on electrochemical dehydrogenation from benzylaniline at a low temperature (for example, room temperature) without applying heat.

SUMMARY

One non-limiting and exemplary embodiment provides a hydrogen desorption method for desorbing hydrogen from an organic hydride at a low temperature, which has been desired to be developed, and provides a dehydrogenation apparatus.

In one general aspect, the techniques disclosed here feature a hydrogen desorption method that includes a step of bringing a liquid containing an alicyclic saturated hydrocarbon having a tertiary carbon atom bearing a saturated hydrocarbon side chain, a quinone, and an electrolyte into contact with a anode and a step of desorbing hydrogen from the alicyclic saturated hydrocarbon having a tertiary carbon atom bearing a saturated hydrocarbon side chain.

In the hydrogen desorption method and the dehydrogenation apparatus of the present disclosure, hydrogen can be desorbed from an alicyclic saturated hydrocarbon having a tertiary carbon atom bearing a saturated hydrocarbon side chain at low temperature.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 11 is a diagram illustrating an example of the dehydrogenation apparatus of the Embodiment 2;

DETAILED DESCRIPTION

Figure 1:
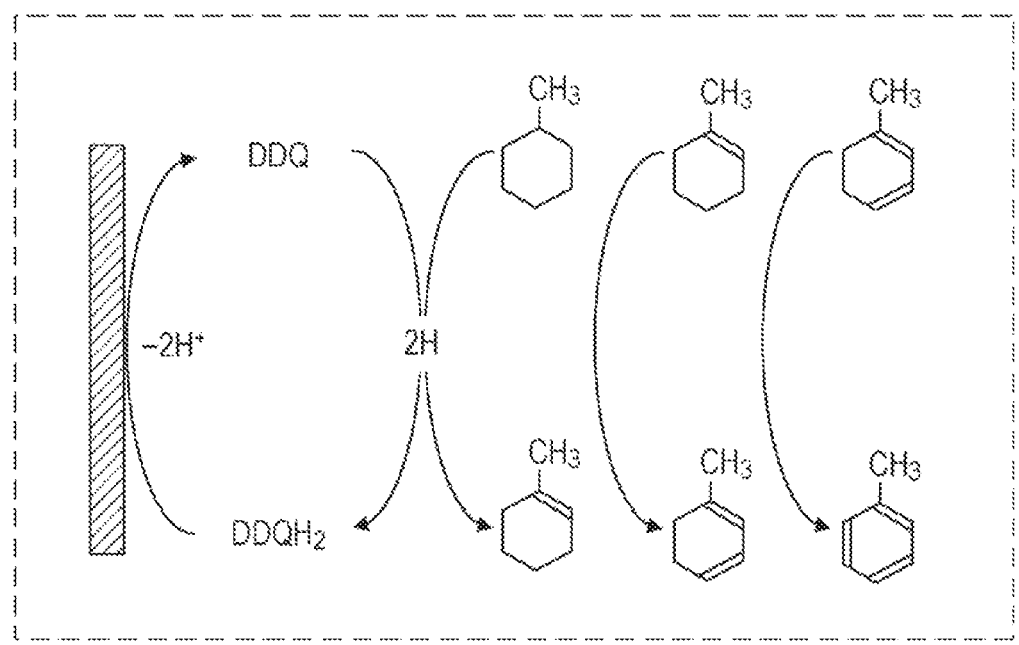
FIG. 1 is a diagram illustrating a reaction in the hydrogen desorption method of the present disclosure.

The outline of the hydrogen desorption method and the dehydrogenation apparatus of the present disclosure are as follows.

The hydrogen desorption method of a first aspect of the present disclosure includes a step of bringing a liquid containing an alicyclic saturated hydrocarbon having a tertiary carbon atom bearing a saturated hydrocarbon side chain, a quinone, and an electrolyte into contact with a anode, and a step of desorbing hydrogen from the alicyclic saturated hydrocarbon having a tertiary carbon atom bearing a saturated hydrocarbon side chain.

In the hydrogen desorption method of a second aspect of the present disclosure, the liquid in the hydrogen desorption method according to the first aspect may further contain a polar solvent.

In the hydrogen desorption method of a third aspect of the present disclosure, the alicyclic saturated hydrocarbon in the hydrogen desorption method according to the first or second aspect may be at least one of a monocyclic saturated hydrocarbon having a tertiary carbon atom bearing a saturated hydrocarbon and a polycyclic saturated hydrocarbon.

In the hydrogen desorption method of a fourth aspect of the present disclosure, the monocyclic saturated hydrocarbon having a tertiary carbon atom bearing a saturated hydrocarbon in the third aspect may contain at least one selected from the group consisting of methylcyclohexane and dimethylcyclohexane.

In the hydrogen desorption method of a fifth aspect of the present disclosure, the quinone in the hydrogen desorption method according to any one of the first to fourth aspects may contain 2,3-dichloro-5,6-dicyano-p-benzoquinone.

In the hydrogen desorption method of a sixth aspect of the present disclosure, the quinone in the hydrogen desorption method according to any one of the first to fourth aspects may contain chloranil.

In the hydrogen desorption method of a seventh aspect of the present disclosure, the hydrogen desorption method according to any one of the first to sixth aspects, hydrogen is desorbed from the alicyclic saturated hydrocarbon by applying a voltage between the anode and an cathode.

In the hydrogen desorption method of a eighth aspect of the present disclosure, the hydrogen may be desorbed from the alicyclic saturated hydrocarbon by applying a direct voltage of 0.07 V or more to the anode with a single cell in the hydrogen desorption method according to the seventh aspect.

In dehydrogenation of an alicyclic saturated hydrocarbon having a tertiary carbon atom bearing a saturated hydrocarbon side chain, the electric power necessary for the dehydrogenation is decreased with decreasing the voltage applied between electrodes. In the case of using chloranil, the dehydrogenation can proceed with a lower application voltage compared to the case using 2,3-dichloro-5,6-dicyano-p-benzoquinone. In the case of using chloranil, the dehydrogenation can proceed by applying, for example, a low direct voltage of about 0.07 V to the anode with a single cell, and it is possible to improve the efficiency of the dehydrogenation.

In the hydrogen desorption method of an ninth aspect of the present disclosure, the hydrogen may be desorbed from the alicyclic saturated hydrocarbon by applying the voltage applied between the anode and the cathode may be a direct voltage of 1.5 V or less applied with a single cell in the hydrogen desorption method according to any one of the first to eighth aspects.

If a direct voltage of, for example, higher than 1.5 V is applied with a single cell, electrolysis of water may consume electric power. Such a case decreases the efficiency of the dehydrogenation of an alicyclic saturated hydrocarbon having a tertiary carbon atom bearing a saturated hydrocarbon side chain. Accordingly, the dehydrogenation apparatus according to this aspect can prevent a decrease in the efficiency of the dehydrogenation by restricting the application voltage of the voltage application device to, for example, 1.5 V or less with a single cell.

In the hydrogen desorption method of a 10th aspect of the present disclosure, the hydrogen desorption method according to any one of the first to ninth aspects may further include a step of conducting the hydrogen desorbed on the anode to the cathode via a polymer electrolyte film.

Even if the conduction of hydrogen is performed using a solid polymer electrolyte film showing proton conductivity in a wet state as a proton conductor, as described above, an n-mer (n≥1) of chloranil, which is insensitive to water, can be used as a mediator.

In the hydrogen desorption method of a 11th aspect of the present disclosure, the hydrogen desorption method according to the 10th aspect may further include a step of supplying a cathode fluid to the cathode and a step of humidifying the cathode fluid.

The solid polymer electrolyte film can be appropriately maintained in a wet state by humidifying the cathode fluid.

The dehydrogenation apparatus of an 12th aspect of the present disclosure includes a liquid containing a quinone, an electrolyte, and an alicyclic saturated hydrocarbon having a tertiary carbon atom bearing a saturated hydrocarbon side chain; an storage chamber containing the liquid; a anode being in contact with the liquid in the storage chamber; and an cathode.

In the dehydrogenation apparatus of a 13th aspect of the present disclosure, the liquid in the dehydrogenation apparatus according to the 12th aspect may further contain a polar solvent.

In the dehydrogenation apparatus of the 14th aspect of the present disclosure, the alicyclic saturated hydrocarbon in the dehydrogenation apparatus according to the 12th or 13th aspect may be at least one of a monocyclic saturated hydrocarbon having a tertiary carbon atom bearing a saturated hydrocarbon and a polycyclic saturated hydrocarbon.

In the dehydrogenation apparatus of a 15th aspect of the present disclosure; the monocyclic saturated hydrocarbon having a tertiary carbon atom bearing a saturated hydrocarbon in the dehydrogenation apparatus according to the 14th aspect may contain at least one selected from the group consisting of methylcyclohexane and dimethylcyclohexane.

In the dehydrogenation apparatus of a 16th aspect of the present disclosure; the quinone in the dehydrogenation apparatus according to any one of the 12th to 15th aspects may contain 2,3-dichloro-5,6-dicyano-p-benzoquinone.

In the dehydrogenation apparatus of a 17th aspect of the present disclosure, the quinone in the dehydrogenation apparatus according to any one of the 12th to 15th aspects may contain chloranil.

In the dehydrogenation apparatus of a 18th aspect of the present disclosure, in the dehydrogenation apparatus according to any one of the 12th to 17th aspects may contain chloranil, further includes a voltage application device applying a voltage between the anode and the cathode.

In the dehydrogenation apparatus of a 19th aspect of the present disclosure, the dehydrogenation apparatus according to the 18th aspect may further include a voltage application device applying a voltage between the anode and the cathode, wherein the voltage application device may apply a direct voltage of 0.07 V or more between the anode and the cathode with a single cell.

In dehydrogenation of an organic hydride, the electric power necessary for the dehydrogenation of an organic hydride is decreased with decreasing the application voltage by the voltage application device. Accordingly, if the dehydrogenation of an organic hydride can proceed even by applying a low direct voltage of, for example, about 0.07 V to a anode with a single cell, it is possible to improve the efficiency of the dehydrogenation of an organic hydride.

In the dehydrogenation apparatus of an 20th aspect of the present disclosure, the dehydrogenation apparatus according to any one of the 12th to 19th aspects may further include a voltage application device applying a voltage between the anode and the cathode, wherein the voltage application device may apply a direct voltage of 1.5 V or less with a single cell.

If a direct voltage of, for example, higher than 1.5 V is applied with a single cell, electrolysis of water may consume electric power. Such a case decreases the efficiency of the dehydrogenation of an alicyclic saturated hydrocarbon having a tertiary carbon atom bearing a saturated hydrocarbon side chain. Accordingly, in the dehydrogenation apparatus according to this aspect, a decrease in the efficiency of the dehydrogenation can be prevented by restricting the application voltage of the voltage application device to, for example, 1.5 V or less with a single cell.

In the dehydrogenation apparatus of a 21th aspect of the present disclosure, the hydrogen desorption apparatus according to any one of the 12th to 20th aspects may further include a proton conductor between the anode and the cathode, wherein the proton conductor may be a solid polymer electrolyte film.

Even if the proton conductor is a solid polymer electrolyte film showing proton conductivity in a wet state, as described above, an n-mer (n≥1) of chloranil, which is insensitive to water, can be used as a mediator.

In the dehydrogenation apparatus of a 22th aspect of the present disclosure, the dehydrogenation apparatus according to the 21th aspect may include a humidifier humidifying the cathode fluid to be supplied to the cathode.

The solid polymer electrolyte film can be appropriately maintained in a wet state by humidifying the cathode fluid with the humidifier.

Embodiments of the hydrogen desorption method and the dehydrogenation apparatus of the present disclosure will now be described with reference to the drawings.

The embodiments described below all show comprehensive or specific examples. The numbers, shapes, materials, components, arrangement configuration and connection configuration of the components, etc. shown in the following embodiments are merely examples and are not intended to limit the present disclosure. Among the components in the following embodiments, components that are not mentioned in any independent claim describing the broadest concept will be described as optional components. In the drawings, descriptions for components denoted by the same signs may be omitted. The drawings schematically illustrate each component for easier understanding, and, for example, the shapes and sizes are not exactly shown in some cases.

Embodiment 1

The hydrogen desorption method of this embodiment uses 2,3-dichloro-5,6-dicyano-p-benzoquinone as an example of the quinone and electrochemically dehydrogenates an alicyclic saturated hydrocarbon having a tertiary carbon atom bearing a saturated hydrocarbon side chain.

(1) Step of Supplying Hydrogen Storage Solution to Electrode

A hydrogen storage solution containing an alicyclic saturated hydrocarbon having a tertiary carbon atom bearing a saturated hydrocarbon side chain, 2,3-dichloro-5,6-dicyano-p-benzoquinone, and an electrolyte is prepared.

The alicyclic saturated hydrocarbon having a tertiary carbon atom bearing a saturated hydrocarbon side chain may be a monocyclic saturated hydrocarbon having a tertiary carbon atom bearing a saturated hydrocarbon side chain or a polycyclic saturated hydrocarbon. Alternatively, the alicyclic saturated hydrocarbon having a tertiary carbon atom bearing a saturated hydrocarbon side chain may be a compound in a hydrogen-storing state by binding of hydrogen to an aromatic hydrocarbon. The term "tertiary carbon atom" refers to a carbon atom in which three of the four bonds are bound to carbon atoms. As described in detail below, in an alicyclic saturated hydrocarbon having a tertiary carbon atom, the reaction proceeds as follows. The hydrogen atoms bound to the tertiary carbon atom are first desorbed, and hydrogen atoms are sequentially desorbed from the alicyclic saturated hydrocarbon. The alicyclic saturated hydrocarbon contains at least one tertiary carbon atom and may contain two or more tertiary carbon atoms.

Examples of the monocyclic saturated hydrocarbon having a tertiary carbon atom bearing a saturated hydrocarbon side chain include methylcyclohexane, 1,2-dimethylcyclohexane, 1,3-dimethylcyclohexane, and 1,4-dimethylcyclohexane. Examples of the polycyclic saturated hydrocarbon include decalin, methyldecalin, 1,2-dimethyldecalin, 1,3-dimethyldecalin, and 1,4-dimethyldecalin. As described above, when these compounds are used as hydrogen storing and supplying means, the compound to which hydrogen is bound and the compound from which hydrogen is desorbed are preferred to be capable of being treated as compounds belonging to petroleum, such as gasoline, from the viewpoints of melting point, boiling point, combustibility, explosiveness, toxicity, etc. From these viewpoints, the monocyclic saturated hydrocarbon having a tertiary carbon atom bearing a saturated hydrocarbon side chain is preferably methylcyclohexane or dimethylcyclohexane; and the polycyclic saturated hydrocarbon is preferably decalin. The compounds obtained by desorbing all hydrogen atoms from methylcyclohexane, dimethylcyclohexane, and decalin are toluene, xylene, and naphthalene, respectively.

2,3-Dichloro-5,6-dicyano-p-benzoquinone (hereinafter, abbreviated as DDQ) is one of oxidants that are used in dehydrogenation extracting hydrogen from organic compounds. Under mild conditions, such as normal temperature and normal pressure, DDQ is difficult to extract a hydrogen atom (hydride) from a tertiary carbon atom. That is, under mild conditions, even if DDQ is used, dehydrogenation of an alicyclic saturated hydrocarbon having a tertiary carbon atom bearing a saturated hydrocarbon side chain is hardly caused. However, in the embodiment, DDQ is inferred to be modified to a higher active state as an oxidant by being electrochemically oxidized. Consequently, a hydrogen atom (hydride) can be extracted from the tertiary carbon atom of an alicyclic saturated hydrocarbon having a tertiary carbon atom bearing a saturated hydrocarbon side chain. Accordingly, electrochemical oxidation of DDQ allows extraction of hydrogen from an alicyclic saturated hydrocarbon having a tertiary carbon atom bearing a saturated hydrocarbon side chain by dehydrogenation. DDQ binds to hydrogen extracted by the dehydrogenation to generate a hydroquinone body. The generated hydroquinone body is electrochemically oxidized to return to DDQ. Therefore, DDQ functions as a mediator in an indirect electrolysis.

The electrolyte provides electric conductivity to the hydrogen storage solution for electrochemically performing oxidation of DDQ and the generated hydroquinone body of DDQ. Examples of the electrolyte include tetraethylammonium tetrafluoroborate, lithium perchlorate, sodium perchlorate, lithium borofluoride, lithium hexafluorophosphate, lithium hexafluoroantimonate, lithium thiocyanate, lithium chloride, lithium trifluoromethane sulfonate, and lithium hexafluoroarsenate.

The hydrogen storage solution may further contain a solvent for increasing the concentration of the electrolyte and realizing high electric conductivity. The solvent is preferably a polar solvent. Examples of the polar solvent include acetonitrile, tetrahydrofuran, 2-methyltetrahydrofuran, nitromethane, dimethylformamide, dimethylsulfoxide, sebaconitrile, nonadecanenitrile, propionitrile, and hexanenitrile.

The amount of the alicyclic saturated hydrocarbon having a tertiary carbon atom bearing a saturated hydrocarbon side chain in the hydrogen storage solution is, for example, 50 vol % or more and 80 vol % or less. The concentration of the electrolyte in the hydrogen storage solution is, for example, 0.1 mol/L or more and 1 mol/L or less.

The hydrogen storage solution can be prepared by weighing an alicyclic saturated hydrocarbon having a tertiary carbon atom bearing a saturated hydrocarbon side chain, DDQ, an electrolyte, and optionally a solvent and mixing them.

The hydrogen storage solution is contained in a container and is in contact with a anode in this container.

(2) Step of Desorbing Hydrogen

Hydrogen is desorbed from an alicyclic saturated hydrocarbon by applying a voltage to the hydrogen storage solution. Specifically, a hydrogen storage solution is put in an appropriate container, an anode and a cathode are immersed in the hydrogen storage solution, and a voltage of 0.1 V or more and 1 V or less is applied to the anode and the cathode. As the anode and the cathode, electrodes that are generally used in electrochemical reactions, such as Pt, C, and Au electrodes, can be selected. In particular, Pt electrodes are preferred.

FIG. 1 collectively shows the reactions in the step of desorbing hydrogen. The first dehydrogenation is shown in Formula (1).

FIG. 1 and Formula (1) show methylcyclohexane as an example of a monocyclic saturated hydrocarbon having a tertiary carbon atom bearing a saturated hydrocarbon side chain.

Application of a voltage of 0.1 V or more and 1 V or less to the hydrogen storage solution seems to oxidize DDQ to generate activated DDQ. Herein, the voltage is, for example, a direct voltage to be applied between a pair of electrodes made of the same material. The activated DDQ extracts a hydrogen atom having reactivity higher than that of the DDQ and being most easily extracted in the monocyclic saturated hydrocarbon having a tertiary carbon atom bearing a saturated hydrocarbon side chain. That is, the DDQ extracts a hydrogen atom bound to a tertiary carbon atom as a hydride. Subsequently, a proton seems to be extracted from a carbon atom adjacent to the carbon atom from which the hydride is extracted to form a carbon-carbon double bond. Consequently, 1-methylcyclohexene is generated. The extracted hydride and proton are inferred to bind to the oxygen atom of the DDQ to generate a hydroquinone body, $DDQH_2$.

$DDQH_2$ is then electrochemically oxidized to return to DDQ. On this occasion, a hydrogen molecule is inferred to be desorbed.

The regenerated DDQ extracts two hydrogen atoms from 1-methylcyclohexene by the same reaction as that shown in Formula (1). Consequently, a carbon-carbon double bond is formed in the 1-methylcyclohexene to generate methylcyclohexadiene. $DDQH_2$ is electrochemically oxidized to return to DDQ. On this occasion, a hydrogen molecule is inferred to be desorbed.

The regenerated DDQ extracts two hydrogen atoms again from methylcyclohexadiene by the same reaction as that shown in Formula (1). On this occasion, a carbon-carbon double bond is formed in the methylcyclohexadiene to generate toluene. $DDQH_2$ is electrochemically oxidized to return to DDQ. On this occasion, a hydrogen molecule is inferred to be desorbed.

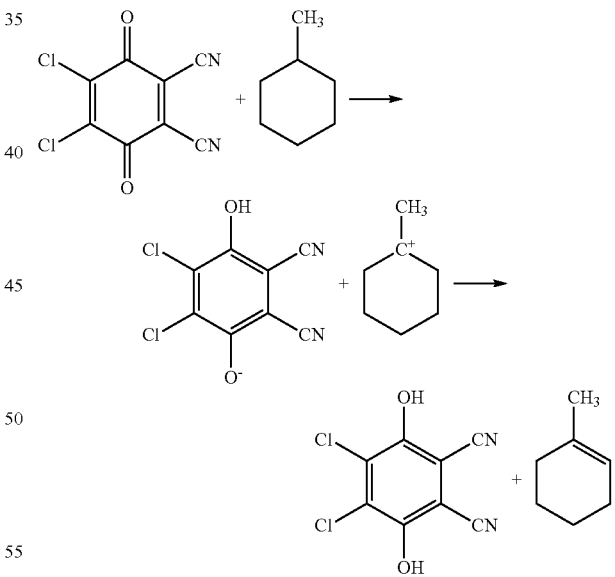

These reactions proceed at normal temperature. That is, in the hydrogen desorption method of the embodiment, hydrogen can be desorbed from an alicyclic saturated hydrocarbon having a tertiary carbon atom bearing a saturated hydrocarbon side chain at normal temperature. Furthermore, the oxidant bound to hydrogen is electrochemically regenerated. On this occasion, hydrogen is inferred to be desorbed to generate a hydrogen molecule. Accordingly, the hydrogen desorption method of the embodiment can desorb hydrogen from an alicyclic saturated hydrocarbon having a tertiary carbon atom bearing a saturated hydrocarbon side chain at temperature lower than that in known methods.

Figure 2:
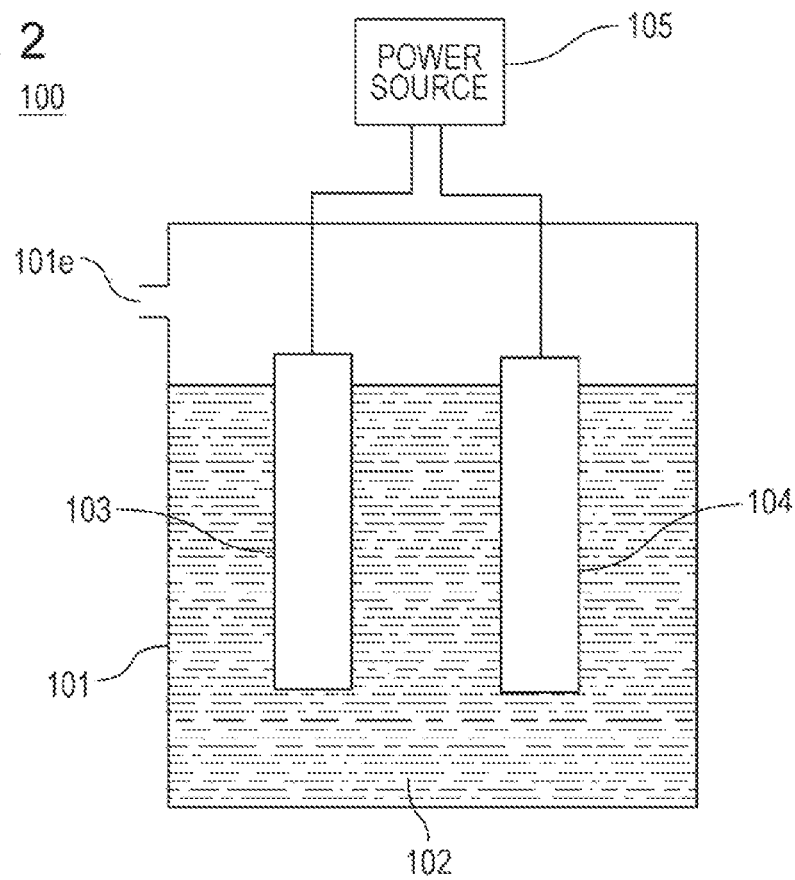
FIG. 2 is a schematic view illustrating an example of the dehydrogenation apparatus of the present disclosure.

FIG. 2 schematically illustrates an example of the dehydrogenation apparatus of the present disclosure. The dehydrogenation apparatus 100 includes a container 101, an cathode 103, a anode 104, and a hydrogen storage solution 102 contained in the container 101. The container 101 is an example of the storage chamber of the present disclosure. The hydrogen storage solution 102 can contain an alicyclic saturated hydrocarbon having a tertiary carbon atom bearing a saturated hydrocarbon side chain. The cathode 103 and the anode 104 are in contact with the hydrogen storage solution 102. The cathode 103 and the anode 104 are electrically connected to a power source 105. The container 101 has an opening 101e. For example, the container 101 is sealed, and only the opening 101e is opened to the outside.

By connecting the cathode 103 and the anode 104 to the power source 105 and applying a voltage between them, according to the hydrogen desorption method of the present disclosure, hydrogen is desorbed from the alicyclic saturated hydrocarbon having a tertiary carbon atom bearing a saturated hydrocarbon side chain to generate hydrogen molecules. The generated hydrogen molecules are released from the opening 101e and can be used as a hydrogen gas.

As described above, the dehydrogenation apparatus of the present disclosure can desorb hydrogen from an alicyclic saturated hydrocarbon having a tertiary carbon atom bearing a saturated hydrocarbon side chain at temperature lower than that in known methods, for example, at normal temperature, and can utilize the desorbed hydrogen as a hydrogen gas.

Although the hydrogen desorption method of the embodiment has been described as an example of extracting six hydrogen atoms from methylcyclohexane and generating toluene, the extraction of hydrogen atoms may be terminated along the way. For example, the hydrogen desorption method may be terminated at the stage when any of 1-methylcyclohexane, methylcyclohexadiene, and toluene is generated from methylcyclohexane.

EXAMPLES

The results of the reaction by the hydrogen desorption method of the present disclosure will now be described.

Example 1

Figure 3:
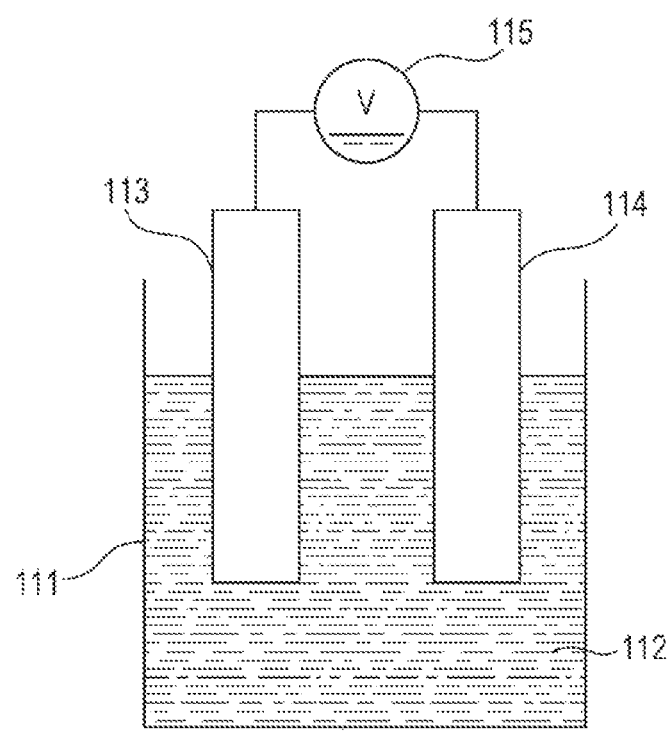
FIG. 3 is a schematic view illustrating an example of the dehydrogenation apparatus used in Examples.

FIG. 3 is a schematic view illustrating an example of the dehydrogenation apparatus 100 used in Examples. As shown in FIG. 3, a 30-mL airtight container 111 was prepared. A mixture of 200 mL of acetonitrile (Wako Pure Chemical Industries, Ltd., 75-05-8), 0.02 moles (concentration after adjustment: 0.1 M) of tetraethylammonium tetrafluoroborate (Tokyo Chemical Industry Co., Ltd., CAS: 429-06-1), 0.0002 moles (concentration after adjustment: 0.001 M) of DDQ (Tokyo Chemical Industry Co., Ltd., 84-58-2), and 0.02 moles (concentration after adjustment: 0.1 M) of methylcyclohexane (in the drawings, referred to as MCH, Wako Pure Chemical Industries, Ltd., 108-87-2) was uniformly mixed by stirring with a stirrer to prepare a sample liquid 112. The prepared sample liquid was introduced into the airtight container 111, and a counter electrode 113 and a work electrode 114 connected to a cyclic voltammetry (CV) device 115 were immersed in the sample liquid. The work electrode 114 and the counter electrode 113 used were a platinum mesh and a platinum bar, respectively. The CV device 115 applied a voltage at a sweep rate of 0.1 V/s such that the potential of the work electrode reached 1 V from −1 V and then returned to −1 V again to perform cyclic voltammetry at normal temperature. The sample liquid 112 was not supplied to gas displacement bubbling.

Example 2

A mixture of 200 mL of acetonitrile, 0.02 moles (concentration after adjustment: 0.1 M) of tetraethylammonium tetrafluoroborate (Tokyo Chemical Industry Co., Ltd., CAS: 429-06-1), 0.0002 moles (concentration after adjustment: 0.001 M) of DDQ (Tokyo Chemical Industry Co., Ltd., 84-58-2), and 0.02 moles (concentration after adjustment: 0.1 M) of 1,2-dimethylcyclohexane (in the drawings, referred to as DMCH) was uniformly mixed by stirring with a stirrer to prepare a sample liquid 112. The prepared sample liquid 112 was introduced into an airtight container 111, and cyclic voltammetry measurement was performed at normal temperature as in Example 1.

Example 3

A mixture of 200 mL of acetonitrile (Wako Pure Chemical Industries, Ltd., 75-05-8), trihexyltetradecylphosphonium bis(trifluoromethylsulfonyl)imide (Sigma-Aldrich Co., Ltd. Purity more than 95%), DDQ (Tokyo Chemical Industry Co., Ltd., 84-58-2), and methylcyclohexane (in the drawings, referred to as MCH, Wako Pure Chemical Industries, Ltd., 108-87-2) was uniformly mixed by stirring with a stirrer to prepare a sample liquid 112.

A concentration of trihexyltetradecylphosphonium bis(trifluoromethylsulfonyl)imide in the sample liquid 112 is 0.1 mol/L. A concentration of DDQ in the sample liquid 112 is 6 mmol/L. A concentration of MCH in the sample liquid 112 is 600 mmol/L. The prepared sample liquid was introduced into the airtight container 111, and a counter electrode 113 (Pt) and a work electrode 114 (Pt) connected to a cyclic voltammetry (CV) device 115 were immersed in the sample liquid. A reference electrode (Pt) is used in the present example. The CV device 115 applied a voltage at a sweep rate of 0.5 V/s such that the potential of the work electrode reached +0.4V from −2.0V to perform cyclic voltammetry at normal temperature. When the sample 112 is stirred and is applied 0.28 V to, a change of concentration of toluene in the sample 112 with respect to a voltage application time is measured by GC (Gas Chromatography). A toluene area ratio is used as a value corresponding to the concentration of toluene. The toluene area ratio is a ratio of an area of toluene to the sum of the area of toluene and an area of MCH. The area of toluene and the area of MCH are measured by GC.

Comparative Example 1

A sample liquid was prepared from acetonitrile, tetraethylammonium tetrafluoroborate, and DDQ only, and cyclic voltammetry measurement was performed at normal temperature as in Example 1.

Comparative Example 2

A mixture of acetonitrile, tetraethylammonium tetrafluoroborate, and 0.02 moles (concentration after adjustment: 0.1 M) of cyclohexane (in the drawings, referred to as CH) was uniformly mixed by stirring with a stirrer to prepare a sample liquid 112. The prepared sample liquid 112 was introduced into an airtight container 111, and cyclic voltammetry measurement was performed at normal temperature as in Example 1.

Results and Discussion

Figure 4:
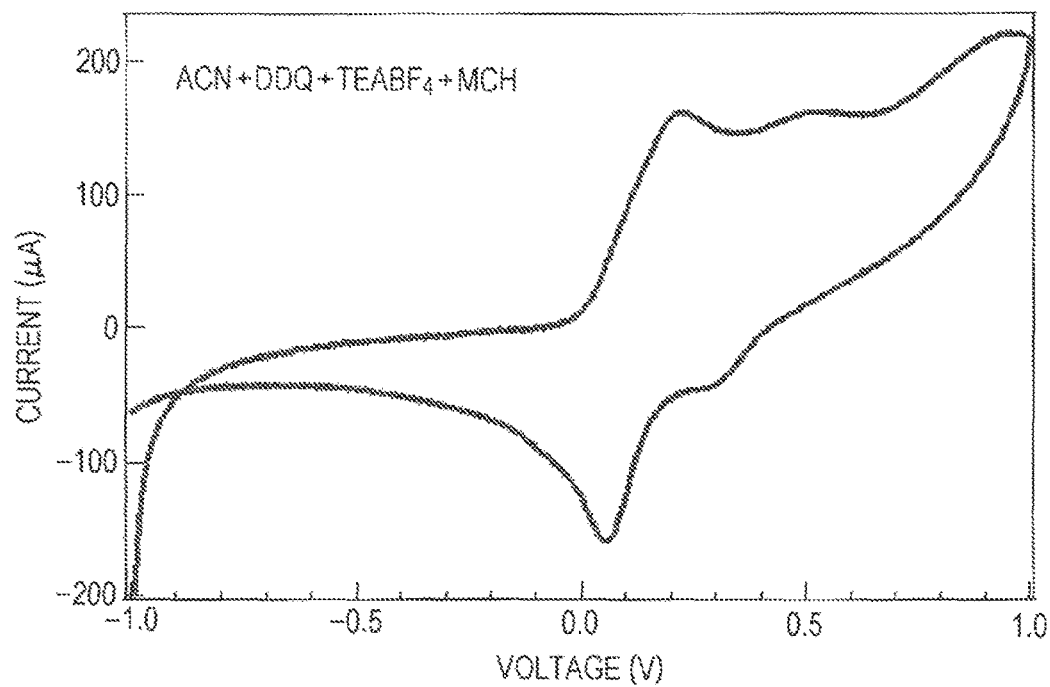
FIG. 4 is an example of a graph showing the results of cyclic voltammetry measurement in Example 1.
Figure 5:
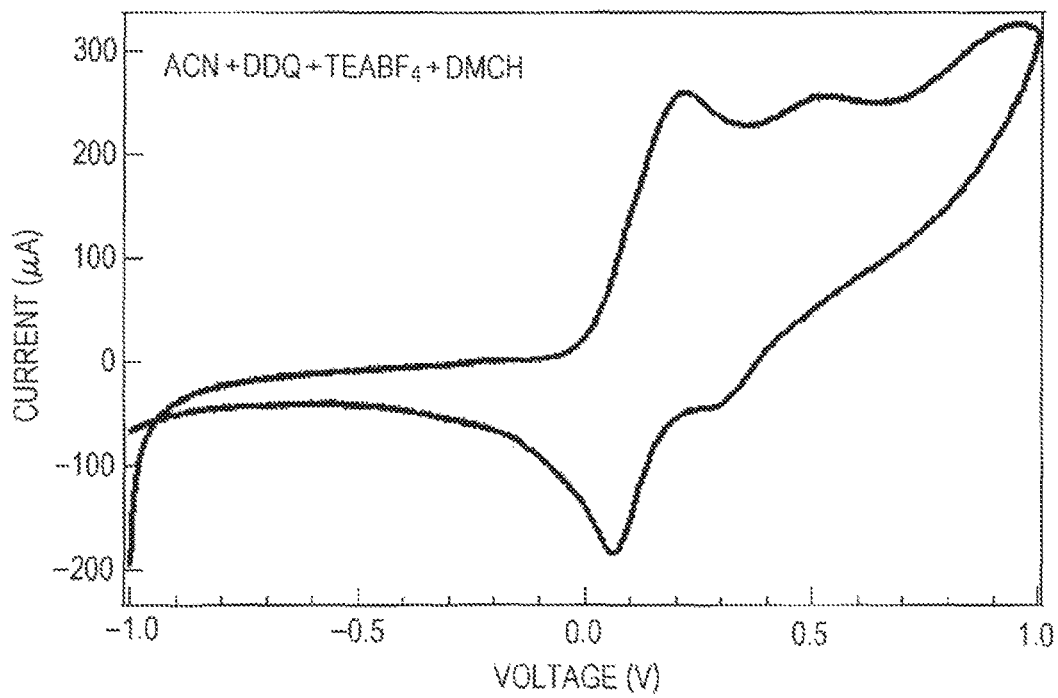
FIG. 5 is an example of a graph showing the results of cyclic voltammetry measurement in Example 2.
Figure 6:
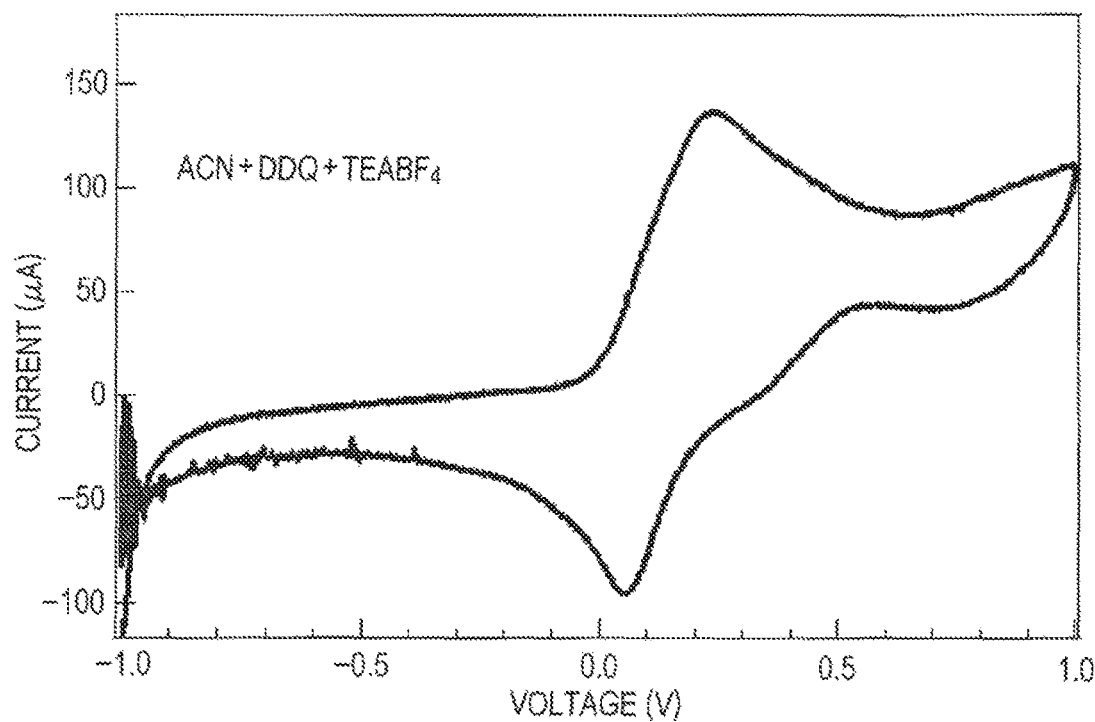
FIG. 6 is an example of a graph showing the results of cyclic voltammetry measurement in Comparative Example 1.
Figure 7:
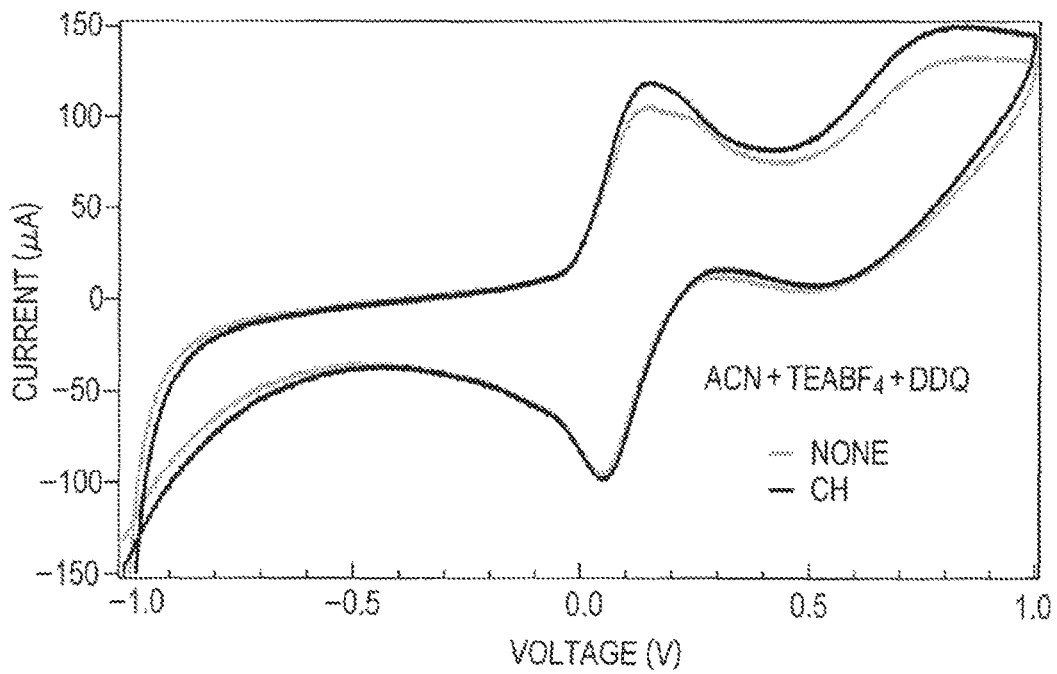
FIG. 7 is an example of a graph collectively showing the results of cyclic voltammetry measurement in Examples 1 and 2 and Comparative Example 1.
Figure 8:
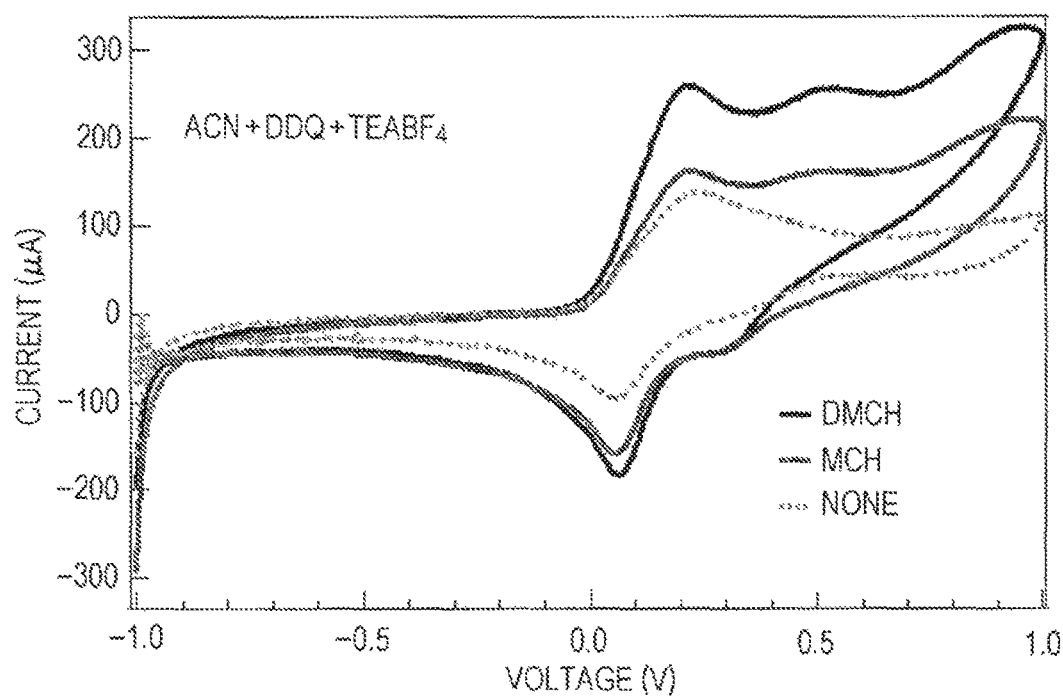
FIG. 8 is an example of a graph collectively showing the results of cyclic voltammetry measurement in Comparative Examples 1 and 2.
Figure 9:
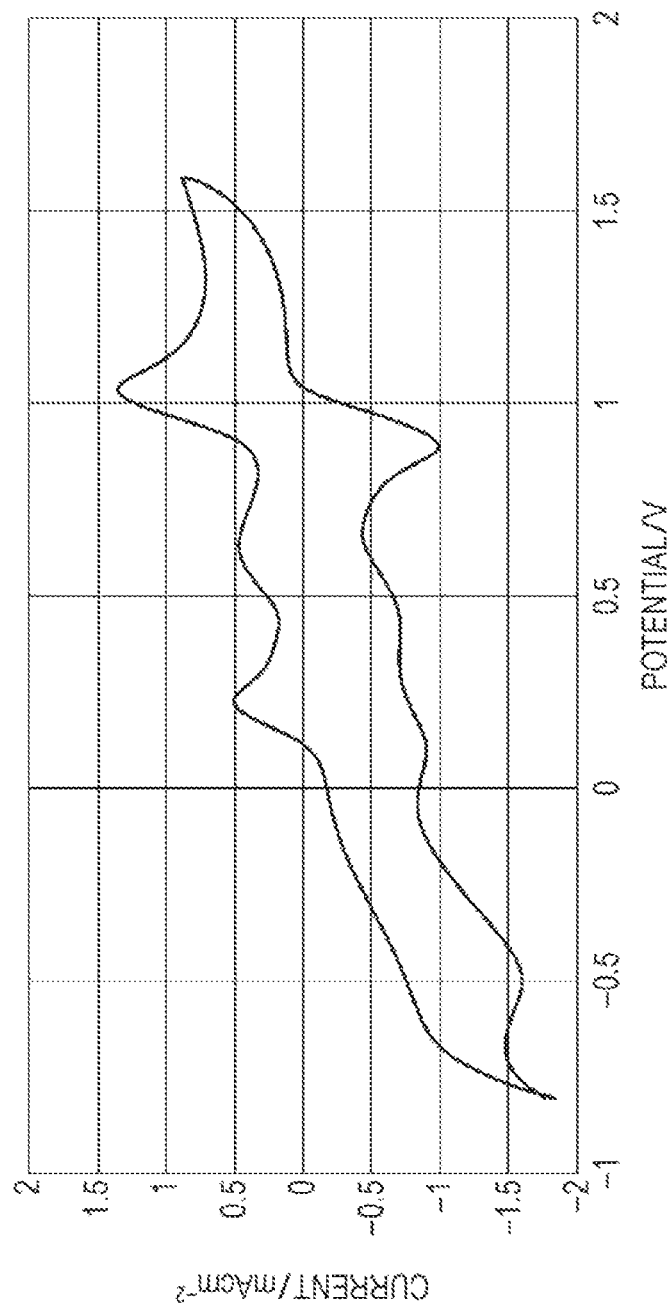
FIG. 9 is an example of a graph collectively showing the results of cyclic voltammetry measurement in Comparative Example 3.
Figure 10:
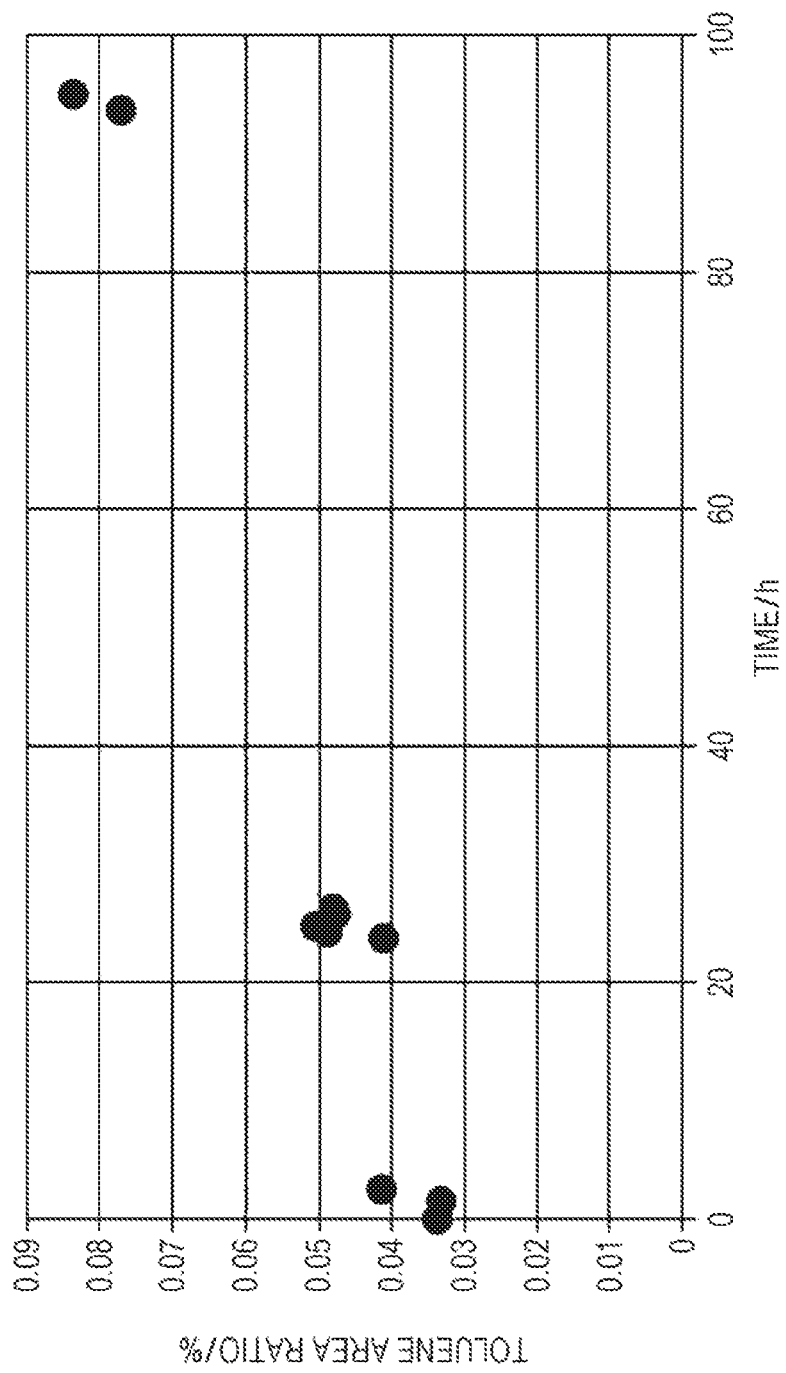
FIG. 10 is an example of a graph collectively showing the results of GC (Gas Chromatography) measurement in Comparative Example 3.

The measurement results of Examples 1 and 2 and Comparative Example 1 are shown in FIGS. 4, 5, and 6, respectively. FIG. 7 collectively shows the measurement results of Comparative Examples 1 and 2, and FIG. 8 collectively shows the measurement results of Examples 1 and 2 and Comparative Example 1. A cyclic voltammetry measurement result in Example 3 is shown in FIG. 9. The measurement results of toluene concentration change are shown in FIG. 10. The result shown in FIG. 9 is modified with standard electrode potential (1.188 V) of the reference electrode (Pt).

As shown in FIGS. 4 and 5, in the samples containing a monocyclic saturated hydrocarbon having a tertiary carbon atom bearing a saturated hydrocarbon side chain of Examples 1 and 2, peaks of oxidation are observed at near 0.2 V and 0.5 V. A large current continues to flow from about 0.2 V to 0.7 V without decreasing the current value, and two peaks are unified. On the reducing side, a peak is observed at near 0.05 V. As shown in FIG. 9, in the sample containing a monocyclic saturated hydrocarbon having a tertiary carbon atom bearing a saturated hydrocarbon side chain of Examples 3, first peaks of oxidation of DDQ are observed at near 0.2 V and 0.6 V, and a second peak of oxidation of DDQ is observed at near 1.0 V. On the reducing side, peaks are observed at near 0.1 V and 0.8 V.

In contrast, in the sample not containing the monocyclic saturated hydrocarbon having a tertiary carbon atom bearing a saturated hydrocarbon side chain of Comparative Example 1, a peak of oxidation is observed at near 0.2 V. This peak turns downward when the voltage exceeds 0.2 V. On the reducing side, a peak is observed at near 0.05 V.

These results suggest that the peak at near 0.2 V is due to the oxidation of DDQ. This peak is consistent with the CV result of DDQ shown in Peter F. Driscoll, Elise Deunf, Leah Rubin, John Arnold, John B. Kerr, Journal of Electron Society, 160 G3152-G3158 (2013).

However, in Examples 1 and 2, the peaks at 0.2 V are larger than that of Comparative Example 1 and are connected to the peaks at 0.5 V without largely decreasing the current value. This seems to indicate that one or more reactions other than the oxidation of DDQ continue to occur. In addition, methylcyclohexane and dimethylcyclohexane are stable compounds and are not oxidized at a voltage of about 0 to 1 V. These results suggest that in the samples of Examples 1 and 2, DDQ in an oxidized form causes dehydrogenation for extracting hydrogen from methylcyclohexane and dimethylcyclohexane at normal temperature to generate carbon-carbon double bonds in the methylcyclohexane and the dimethylcyclohexane. Considering that the current value is not decreased much in a voltage range of 0.2 V to 1 V, the dehydrogenation is inferred to be sequentially caused. In addition, since the current value at 0.2 V is high compared to that in Comparative Example 1, at least a part of DDQ molecules reduced (addition of hydrogen) by contributing to dehydrogenation is inferred to be electrochemically oxidized to return to DDQ. The toluene area ratio is increased with the passage of the voltage application time. It is inferred that MCH undergoes dehydrogenation at room temperature by DDQ in the oxidized form and toluene is formed.

As shown in FIG. 7, the graph of Comparative Example 2 in which cyclohexane is used as a monocyclic saturated hydrocarbon not having a tertiary carbon atom bearing a saturated hydrocarbon side chain is almost consistent with the graph of Comparative Example 1. This seems to indicate that the dehydrogenation described above is not caused in cyclohexane. Since cyclohexane does not have a tertiary carbon atom bearing a saturated hydrocarbon side chain, cyclohexane is inferred not to react with DDQ in an oxidized form.

In Examples 1 and 2, generation of hydrogen was not observed. This is probably caused by the generated hydrogen is occluded in Pt constituting the work electrode or the counter electrode.

Embodiment 2

In an example of generating hydrogen by dehydrogenation of an organic hydride, the work electrode and the counter electrode are separated from each other with, for example, a proton conductor to form a receiver of the electrons obtained by the dehydrogenation of the organic hydride. If the proton conductor needs water for obtaining proton conductivity on this occasion, DDQ used as a mediator reacts with water. That is, the cyano group of DDQ reacts with water to generate hydrogen cyanide, and DDQ is inactivated. Therefore, in such a case, the dehydrogenation of the organic hydride is prevented. Accordingly, if the proton conductor is, for example, a solid polymer electrolyte film, it is necessary to retain the dehydrogenation apparatus in a humidified atmosphere for ensuring proton conductivity. Thus, DDQ cannot be used as a mediator.

Accordingly, the present inventors have diligently studied on the mediator in dehydrogenation of an organic hydride, specifically, an alicyclic saturated hydrocarbon having a tertiary carbon atom bearing a saturated hydrocarbon side chain, and have arrived at the following idea.

That is, the hydrogen desorption method of the embodiment includes a step of bringing a liquid containing an alicyclic saturated hydrocarbon having a tertiary carbon atom bearing a saturated hydrocarbon side chain, a chloranil n-mer (n≥1), and an electrolyte into contact with an anode containing a dehydrogenation catalyst and a step of applying a voltage to the anode to desorb hydrogen from the alicyclic saturated hydrocarbon having a tertiary carbon atom bearing a saturated hydrocarbon side chain.

The dehydrogenation apparatus of the embodiment includes an anode containing a dehydrogenation catalyst, a cathode containing a catalyst for reducing protons, a proton conductor disposed between the anode and the cathode, a first server for supplying a liquid containing an alicyclic saturated hydrocarbon having a tertiary carbon atom bearing a saturated hydrocarbon side chain, a chloranil n-mer (n≥1), and an electrolyte to the anode, and a voltage application device applying a voltage to the anode and the cathode.

As described above, the dehydrogenation apparatus and the hydrogen desorption method of the embodiment can appropriately perform dehydrogenation of an alicyclic saturated hydrocarbon having a tertiary carbon atom bearing a saturated hydrocarbon side chain, compared to the case using DDQ as a mediator.

Specifically, even if the dehydrogenation apparatus is needed to be retained in a humidified atmosphere for ensuring proton conductivity, an n-mer (n≥1) of chloranil, which is insensitive to water, can be used as a mediator.

Use of a chloranil n-mer (n≥1) as a mediator allows dehydrogenation of an alicyclic saturated hydrocarbon having a tertiary carbon atom bearing a saturated hydrocarbon side chain at a low voltage, compared to the case using DDQ as a mediator. Accordingly, the dehydrogenation apparatus and the hydrogen desorption method of the embodiment can reduce the electric power necessary for dehydrogenation of an alicyclic saturated hydrocarbon having a tertiary carbon atom bearing a saturated hydrocarbon side chain, compared to the case using DDQ as a mediator. The details will be described in Example 2.

Apparatus Configuration

FIG. 11 is a diagram illustrating an example of the dehydrogenation apparatus of the embodiment.

In the example shown in FIG. 11, the dehydrogenation apparatus 100 includes an anode 10, a cathode 11, a proton conductor 12, a tank 20, a first server 21, a second server 31, a humidifier 32, and a voltage application device 40.

In the dehydrogenation apparatus 100 of the embodiment, a laminate including the anode 10, the cathode 11, and the proton conductor 12 is disposed so as to divide the inside of the container. The region on the anode 10 side of the container constitutes an anode chamber 15 into which the liquid containing an alicyclic saturated hydrocarbon having a tertiary carbon atom bearing a saturated hydrocarbon side chain, a chloranil n-mer (n≥1), and an electrolyte flows; and the region on the cathode 11 side of the container constitutes a cathode chamber 16 into which a cathode fluid flows, but the configuration is not limited thereto. For example, in this example, the cathode fluid is humidified for maintaining the proton conductor 12 in a wet state, but the proton conductor 12 may be maintained in a wet state by supplying moisture from the anode 10 side. In such a case, the cathode fluid is not necessarily allowed to flow into the cathode chamber 16. The anode chamber 15 is an example of the storage chamber of the present disclosure.

The anode 10 is an electrode containing a dehydrogenation catalyst and may have any configuration as long as it contains a dehydrogenation catalyst. As the catalytic metal of the dehydrogenation catalyst, for example, platinum (Pt) can be used, but the catalytic metal is not limited thereto. Examples of the carrier of the catalyst include carbon.

The cathode 11 is an electrode containing a catalyst for reducing protons and may have any configuration as long as it contains a catalyst for reducing protons. As the catalytic metal of the catalyst for reducing protons, for example, platinum (Pt) and ruthenium (Ru) can be used, but the catalytic metal is not limited thereto. Examples of the carrier of the catalyst include carbon.

The proton conductor 12 is disposed between the anode 10 and the cathode 11. Specifically, the anode 10 is disposed on one of the main surfaces of the proton conductor 12, and the cathode 11 is disposed on the other main surface of the proton conductor 12.

The proton conductor 12 may have any configuration as long as it is a member having proton conductivity.

Examples of the proton conductor 12 include solid polymer electrolyte films, such as Nafion (registered trademark, manufactured by E.I. du Pont Nemours and Company) and capping electrolyte films.

Examples of the proton conductor 12 include inorganic electrolyte films, such as films of yttrium-doped barium zirconate (BZY), a compound composed of iron and tantalum, or a compound mainly composed of stannous pyrophosphate; and inorganic-organic hybrid electrolyte films composed of porous inorganic materials and ionic liquids absorbed therein.

The first server 21 supplies a liquid containing an alicyclic saturated hydrocarbon having a tertiary carbon atom bearing a saturated hydrocarbon side chain, a chloranil n-mer (n≥1), and an electrolyte (hereinafter, occasionally abbreviated to "organic hydride solution") to the anode 10.

The tank 20 contains an organic hydride solution. The organic hydride solution may contain a polar solvent, such as acetonitrile and water, and may be mixed with the aromatic compound generated by dehydrogenation of the organic hydride.

The first server 21 may have any configuration as long as it can supply the above-described liquid to the anode 10. Examples of the first server 21 include a positive displacement pump.

The alicyclic saturated hydrocarbon having a tertiary carbon atom bearing a saturated hydrocarbon side chain in the organic hydride solution may be an alicyclic saturated hydrocarbon in a hydrogen-storing state by binding of hydrogen to an aromatic hydrocarbon having a saturated hydrocarbon side chain.

The alicyclic saturated hydrocarbon having a tertiary carbon atom bearing a saturated hydrocarbon side chain may be a monocyclic saturated hydrocarbon having a tertiary carbon atom bearing a saturated hydrocarbon side chain or a polycyclic saturated hydrocarbon.

The monocyclic saturated hydrocarbon having a tertiary carbon atom bearing a saturated hydrocarbon side chain is, for example, methylcyclohexane, 1,2-dimethylcyclohexane, 1,3-dimethylcyclohexane, or 1,4-dimethylcyclohexane. The polycyclic saturated hydrocarbon is, for example, decalin, methyldecalin, 1,2-dimethyldecalin, 1,3-dimethyldecalin, or 1,4-dimethyldecalin. As described above, when these compounds are used as hydrogen storing and supplying means, the compound to which hydrogen is bound and the compound from which hydrogen is desorbed are preferred to be capable of being treated as compounds belonging to petroleum; such as gasoline, from the viewpoints of melting point, boiling point, combustibility; explosiveness; toxicity, etc. From these viewpoints, the monocyclic saturated hydrocarbon having a tertiary carbon atom bearing a saturated hydrocarbon side chain is preferably methylcyclohexane or dimethylcyclohexane, and the polycyclic saturated hydrocarbon is preferably decalin. The compounds obtained by desorbing all hydrogen atoms from methylcyclohexane, dimethylcyclohexane, and decalin are toluene; xylene, and naphthalene, respectively.

Figure 12A:
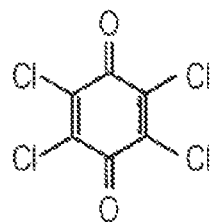
FIGS. 12A to 12C are diagrams illustrating examples of the structural formula of a chloranil n-mer (n≥1) in an organic hydride solution.
Figure 12B:
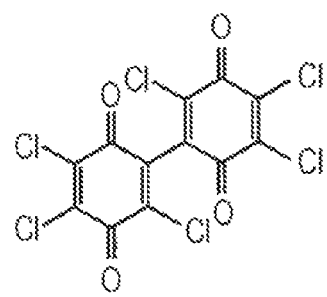
Figure 12C:
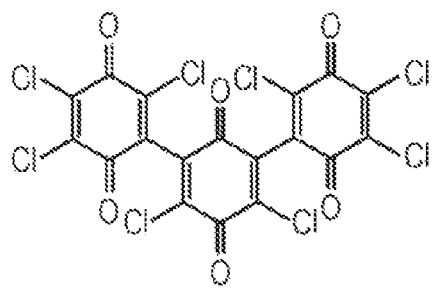

FIGS. 12A to 12O are diagrams illustrating examples of structural formula of a chloranil n-mer (n≥1) in an organic hydride solution. FIG. 12A shows the structural formula of a chloranil monomer; FIG. 12B shows the structural formula of a chloranil dimer; and FIG. 12O shows the structural formula of a chloranil trimer.

The chloranil n-mer (n≥1) in the organic hydride solution functions as a mediator in indirect electrolysis.

Figure 13A:
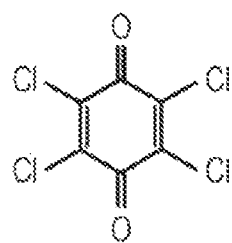
FIGS. 13A and 13B are diagrams illustrating an example of chloranil and an example of hydrogenated chloranil, hydroquinone, respectively.
Figure 13B:
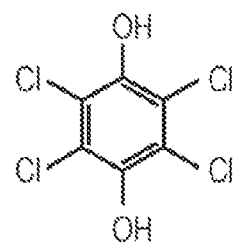

The function of chloranil as a mediator will now be described using a chloranil monomer (hereinafter, referred to as chloranil) as an example of the chloranil n-mer (n≥1) with reference to FIGS. 13A and 13B.

Chloranil (see FIG. 13A) is inferred to be activated by being electrochemically oxidized compared to that before the oxidation. The activated chloranil can extract hydrogen from an organic hydride by dehydrogenation. The activated chloranil seems to then bind to the extracted hydrogen to generate a hydroquinone body (see FIG. 13B). The hydroquinone body of chloranil seems to be then electrochemically oxidized to return to chloranil, and hydrogen seems to be desorbed from the hydroquinone body.

The reactions described above proceed at low temperature (for example, room temperature). That is, the dehydrogenation apparatus 100 of the embodiment can desorb hydrogen from an alicyclic saturated hydrocarbon having a tertiary carbon atom bearing a saturated hydrocarbon side chain at low temperature. In addition, hydrogen desorption of the hydroquinone body of chloranil at low temperature allows electrochemical regeneration of chloranil.

The electrolyte in the organic hydride solution is a material capable of forming an electric double layer when a voltage is applied to the organic hydride solution. The electrolyte may be any material that can form an electric double layer when a voltage is applied to the organic hydride solution. An electrolytic solution can be prepared by, for example, dissolving an electrolyte in a polar solvent, and examples thereof include electrolyte-containing water and ionic liquid.

Examples of the electrolyte include, but not limited to, trihexyltetradecylphosphonium bis(trifluoromethylsulfonyl) imide.

The second server 31 supplies cathode fluid to the cathode 11 and may have any configuration as long as it can supply cathode fluid to the cathode 11.

When the proton conductor 12 is, for example, a solid polymer electrolyte film, the solid polymer electrolyte film shows proton conductivity in a wet state. Accordingly, in this case, the dehydrogenation apparatus 100 includes a humidifier 32 for humidifying the cathode fluid. The humidifier 32 may have any configuration as long as it can humidify the cathode fluid.

For example, in the dehydrogenation apparatus 100 of the embodiment, a bubbling system is used for humidifying the cathode fluid. That is, the humidifier 32 includes a bubbling tank (not shown) for containing water for the liquid. The cathode fluid is allowed to pass through the water in the bubbling tank and is thereby humidified. In such a case, the second server 31 is a device for adjusting the flow rate of a carrier gas when supplied to the water in the bubbling tank of the bubbling system. Examples of the second server 31 include a massflow controller and a flow regulating valve.

When an inert gas is used as the carrier gas of the bubbling system, the cathode fluid includes the inert gas. Examples of the inert gas include a nitrogen gas and noble gases such as an argon gas.

As described above, in the dehydrogenation apparatus 100 of the embodiment, the cathode fluid is humidified by being bubbled into water and is then supplied from the humidifier 32 and passes through the cathode chamber 16 to come into contact with the cathode 11. Consequently, moisture in the cathode fluid is supplied to the proton conductor 12 from the cathode 11. The cathode fluid is thus actively humidified to appropriately maintain the proton conductor 12 (for example, solid polymer electrolyte film) in a wet state.

The voltage application device 40 applies a voltage to the anode 10 and the cathode 11. Specifically, the high-potential side terminal of the voltage application device 40 is connected to the anode 10, and the low-potential side terminal of the voltage application device 40 is connected to the cathode 11. The voltage application device 40 may have any configuration as long as it can apply a desired voltage between the anode 10 and the cathode 11.

For example, the voltage application device 40 may apply a direct voltage of 0.07 V or more to the anode 10 with a single cell. In the dehydrogenation of an alicyclic saturated hydrocarbon having a tertiary carbon atom bearing a saturated hydrocarbon side chain, the electric power necessary for dehydrogenation is decreased with decreasing the application voltage of the voltage application device 40. Use of chloranil as the quinone allows the dehydrogenation of an alicyclic saturated hydrocarbon having a tertiary carbon atom bearing a saturated hydrocarbon side chain to proceed even by applying a low direct voltage of about 0.07 V to the anode 10 with a single cell. The efficiency of dehydrogenation can be thus improved.

The voltage application device 40 may apply a direct voltage of 1.5 V or less with a single cell. Application of a direct voltage of, for example, higher than 1.5 V by the voltage application device 40 with a single cell has a risk of consumption of electric power by electrolysis of water. Such consumption decreases the efficiency of the dehydrogenation of the alicyclic saturated hydrocarbon having a tertiary carbon atom bearing a saturated hydrocarbon side chain. Accordingly, in the dehydrogenation apparatus 100 of the embodiment, a decrease in the efficiency of dehydrogenation of an alicyclic saturated hydrocarbon having a tertiary carbon atom bearing a saturated hydrocarbon side chain can be prevented by restricting the application voltage of the voltage application device 40 to, for example, 1.5 V or less with a single cell.

The application voltage of the voltage application device 40 described above is a mere example, and the present disclosure is not limited thereto.

Operation

An example of the hydrogen desorption method (operation of the dehydrogenation apparatus 100) of the embodiment will now be described with reference to FIG. 11.

The following operation of the dehydrogenation apparatus 100 may be performed by a control program of a controller (not shown). However, it is not absolutely necessary to perform the following operation with the controller. An operator may perform a part or the whole of the operation.

The controller may have any configuration as long as it has a controlling function. The controller includes, for example, an arithmetic circuit and a memory device for storing the control program. Examples of the arithmetic circuit include MPU and CPU. Examples of the memory device include a memory. The controller may be constituted of a single controller performing centralized control or may be constituted of a plurality of controllers performing distributed control by cooperation with each other.

The hydrogen desorption method of the embodiment includes a step of supplying a liquid containing an alicyclic saturated hydrocarbon having a tertiary carbon atom bearing a saturated hydrocarbon side chain, a chloranil n-mer (n≥1), and an electrolyte to an anode 10 containing a dehydrogenation catalyst and a step of applying a voltage between the anode and the cathode to desorb hydrogen from the alicyclic saturated hydrocarbon having a tertiary carbon atom bearing a saturated hydrocarbon side chain.

Specifically, an organic hydride solution is supplied to an anode chamber 15 from a tank 20 through a supply pipe, and a cathode fluid containing moisture is supplied to a cathode chamber 16 from a humidifier 32 through a supply pipe.

On this occasion, a predetermined direct voltage is applied between the anode 10 and the cathode 11 with a voltage application device 40. Consequently, hydrogen is desorbed from the alicyclic saturated hydrocarbon having a tertiary carbon atom bearing a saturated hydrocarbon side chain in the organic hydride solution.

In the anode 10, the alicyclic saturated hydrocarbon having a tertiary carbon atom bearing a saturated hydrocarbon side chain in the organic hydride solution releases electrons and hydrogen atoms (protons) to convert to an aromatic compound.

The released electrons move to the cathode 11 via the voltage application device 40. The protons move from the proton conductor 12 to the cathode 11.

In the cathode 11, a reduction reaction of protons and electrons is performed to generate a hydrogen gas.

The organic hydride solution passed through the anode chamber 15 contains the aromatic compound generated by the dehydrogenation of the alicyclic saturated hydrocarbon having a tertiary carbon atom bearing a saturated hydrocarbon side chain and may be returned to the tank 20 through an exhaust pipe as shown in FIG. 11 or may be sent to another tank (not shown). The aromatic compound can be reused as an organic hydride through hydrogenation.

Example 1

In the dehydrogenation apparatus 100 and the hydrogen desorption method of this example, methylcyclohexane (MCH) was used as the monocyclic saturated hydrocarbon having a tertiary carbon atom bearing a saturated hydrocarbon side chain; trihexyltetradecylphosphonium bis(trifluoromethylsulfonyl)imide was used as the electrolyte; chloranil monomer (hereinafter, referred to as chloranil) was used as the mediator; and an argon gas was used as the carrier gas of the bubbling system.

The organic hydride solution contained in the tank 20 was prepared such that the weight ratio of MCH, electrolyte, and chloranil was 62:21:0.1. That is, the organic hydride solution was a high-concentration organic hydride solution prepared by dissolving chloranil in MCH in a liquid form without using a solvent.

The specifications of the evaluation cell were as follows:
proton conductor 12: Nafion NR-21 (thickness: about 50 μm) having an electrode area of 20-mm square,
anode 10: carbon-supported Pt electrode, and
cathode 11: carbon-supported Pt—Ru electrode.

The environmental temperature of the dehydrogenation apparatus 100 was maintained at room temperature. The organic hydride solution was sent to the anode chamber 15 at a flow rate of 2 ccm, and an argon gas humidified by bubbling was sent to the cathode chamber 16 at a flow rate of 200 sccm.

A quadrupole mass spectrometer (not shown) was provided in the exhaust pipe in which the argon gas passed through the cathode chamber 16 flows. The direct voltage applied to the evaluation cell by the voltage application device 40 was gradually increased from 0 V up to 1.1 V.

The experimental conditions described above are mere examples, and the present disclosure is not limited thereto.

Figure 14:
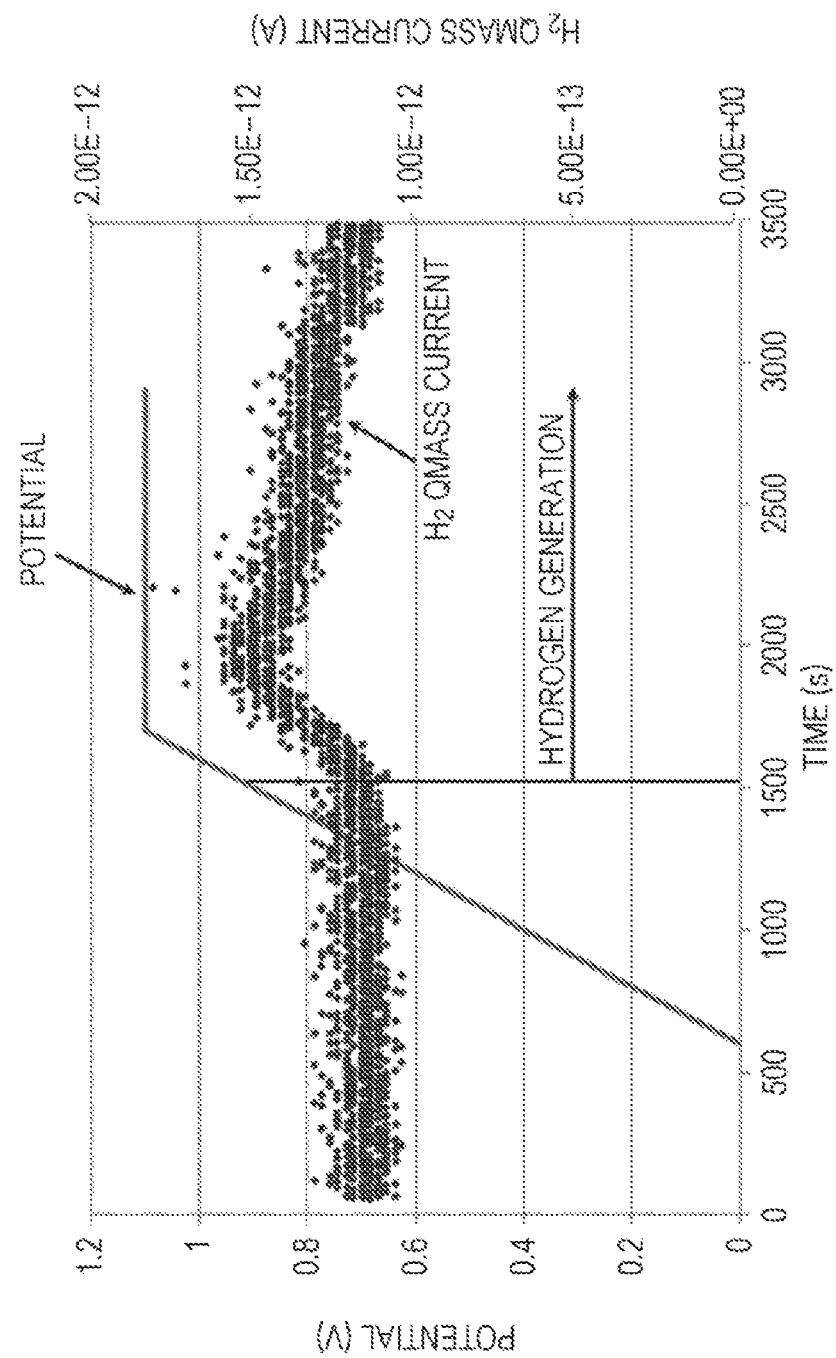
FIG. 14 is a graph showing a relationship between the voltage applied to an evaluation cell and the current value of hydrogen measured with a quadrupole mass spectrometer.

FIG. 14 shows a relationship between the voltage applied to an evaluation cell and the current value of hydrogen measured with a quadrupole mass spectrometer. As shown in FIG. 14, the start of generation of hydrogen by application of a direct voltage of about 0.9 V to the evaluation cell with a single cell was observed by gas analysis with a quadrupole mass spectrometer. In the voltage of 0.9 V applied to the evaluation cell showed the start of generation of hydrogen, the voltage applied for the electrode reaction of the anode 10 was 0.07 V. The voltage applied to the anode 10 for the electrode reaction of the anode 10 was determined by subtracting the sum of the voltage loss due to the film resistance of the proton conductor 12 (Nafion film) and the voltage loss due to the electrode reaction of the cathode 11 from the voltage applied to the evaluation cell. The sum of both voltage losses is the voltage value measured by disposing Pt electrodes on the anode 10 side main surface of the proton conductor 12 and on the opposite side main surface of the proton conductor 12 side of the cathode 11.

Figure 15:
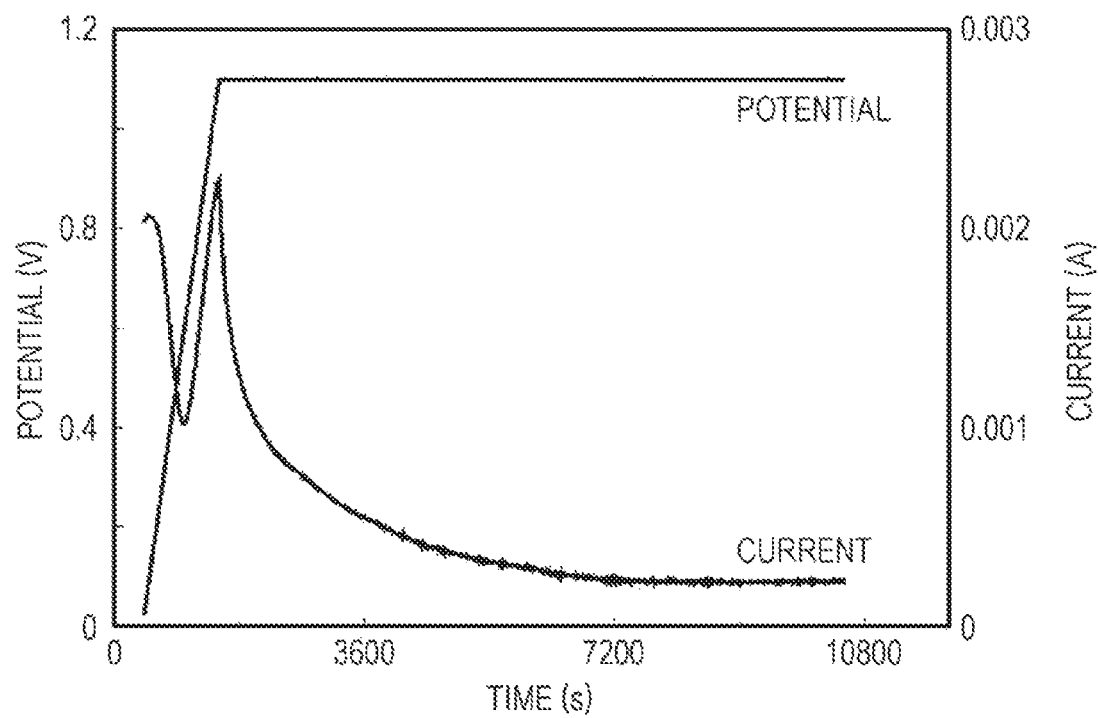
FIG. 15 is a graph showing a relationship between the voltage applied to an evaluation cell and the current flowing in the evaluation cell.

FIG. 15 shows a relationship between the voltage applied to an evaluation cell and the current flowing in the evaluation cell. As shown in FIG. 15, a current continues to flow in the evaluation cell by applying a voltage of 0.9 V or more showing generation of hydrogen in FIG. 14. A relatively high current flowing in the evaluation cell at about 0.9 V and a current flowing in the evaluation cell during application of a voltage of lower than 0.9 V are inferred to be currents that flow when an electric double layer is formed on the electrode surface.

Figure 16:
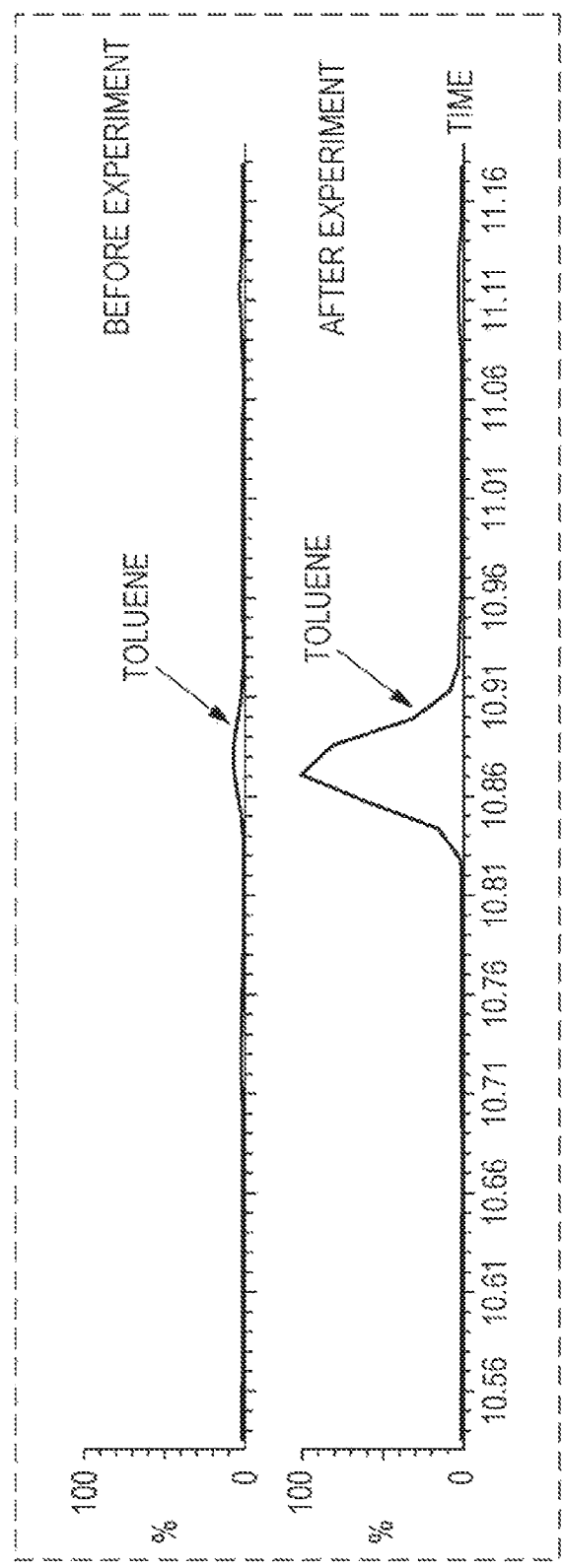
FIG. 16 is a graph showing the results of detection of toluene in the solution in the anode chamber before and after the experiment with a gas chromatograph-mass spectrometer.

FIG. 16 shows the results of detection of toluene in the solution in the anode chamber with a gas chromatograph-mass spectrometer (GC-MS) before and after the experiment. The results after the experiment shown in FIG. 16 are the results of detection of toluene in the solution in anode chamber with a GC-MS, after the experiment shown in FIG. 14 of repeating 30 cycles of application of a voltage to the evaluation cell for 3000 seconds.

As shown in FIG. 16, the amount of toluene in the solution in the anode gas increased after the experiment.

Specifically, the amount of toluene in the solution in the anode chamber 15 detected with a GC-MS before the experiment was 3.9 ppm. The amount of toluene in the solution passed through the anode chamber 15 detected with a GC-MS after the experiment was 60.9 ppm, which was 15-fold that before the experiment. Generation of toluene, which is the product by dehydrogenation of MCH, was confirmed by the experiment described above.

COMPARATIVE EXAMPLE

The experimental conditions of Comparative Example are the same as those of Example 1 except that the organic hydride solution contained in the tank 20 was prepared such that the weight ratio of MCH, electrolyte, and DDQ was 62:21:0.1, and the explanations thereof are omitted.

Application of a direct voltage to the evaluation cell by the voltage application device 40 immediately changed the organic hydride solution to red. That is, DDQ immediately reacted with water. In addition, gas analysis with the quadrupole mass spectrometer did not observe hydrogen in the argon gas.

As described above, the dehydrogenation apparatus 100 and the hydrogen desorption method of this example can appropriately perform dehydrogenation of an organic hydride, compared to the case using DDQ as the mediator. Specifically, even if the dehydrogenation apparatus is needed to be retained in a humidified atmosphere for ensuring proton conductivity, an n-mer (n≤1) of chloranil, which is insensitive to water, can be used as a mediator.

In the dehydrogenation apparatus 100 and the hydrogen desorption method of this example, since the dehydrogenation of an organic hydride proceeds even by applying a low direct voltage of about 0.07 V to the anode 10 with a single cell, the efficiency of dehydrogenation of the organic hydride can be improved.

Example 2

An experiment of comparing the oxidation voltage when chloranil was used as the mediator and the oxidation voltage when DDQ was used as the mediator based on the information obtained by cyclic voltammetry (CV) will now be described.

Conditions for CV Measurement

A solution was prepared by dissolving chloranil (1 mmol/L), an electrolyte (0.1 mol/L), and MCH (20 mmol/L) in a solvent acetonitrile. The solution was put in a glass cell having a diameter of 6 cm and was subjected to CV measurement.

As a comparative example, a solution was prepared by dissolving DDQ (1 mmol/L), an electrolyte (0.1 mol/L), and MCH (20 mmol/L) in a solvent acetonitrile. The solution was put in a glass cell having a diameter of 6 cm and was subjected to CV measurement.

Pt electrodes each having a diameter of 3 mm were used as the work electrode and the counter electrode for the CV measurement, and a wire-type Pt electrode was used as a reference electrode. The scan speed in an application voltage range of −2.4 to 1.6 V was set to 100 mV/sec, and a voltage was applied between the work electrode and the reference electrode.

The conditions for CV measurement described above are mere examples, and the present disclosure is not limited thereto.

Results of CV Measurement

Figure 17:
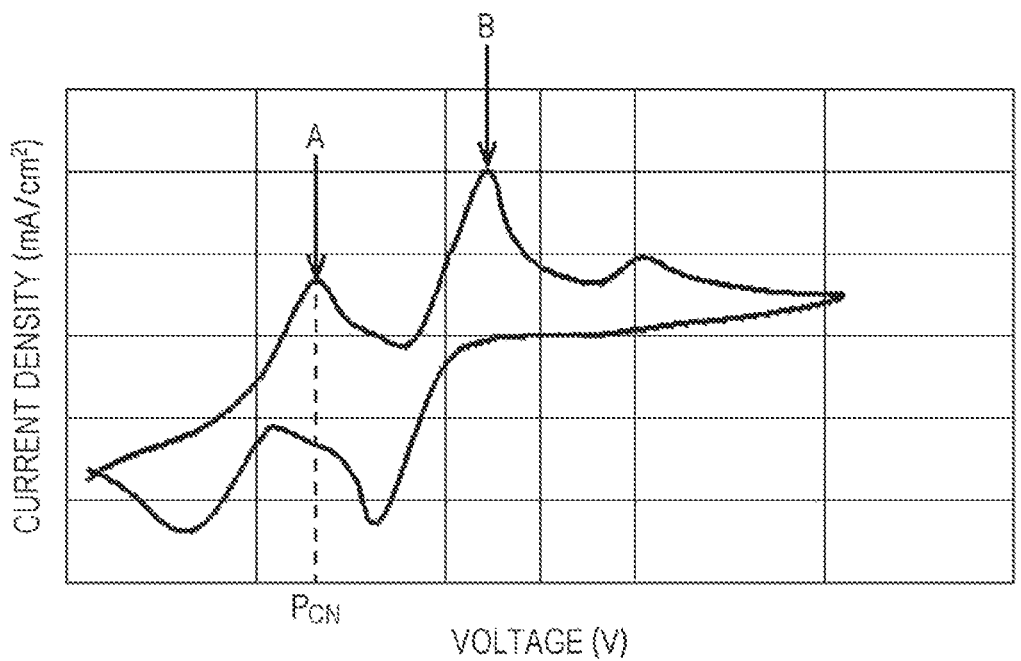
FIG. 17 is a graph showing an example of a current-voltage curve of current voltammetry (CV) measurement of an organic hydride solution when chloranil is used as a mediator.
Figure 18:
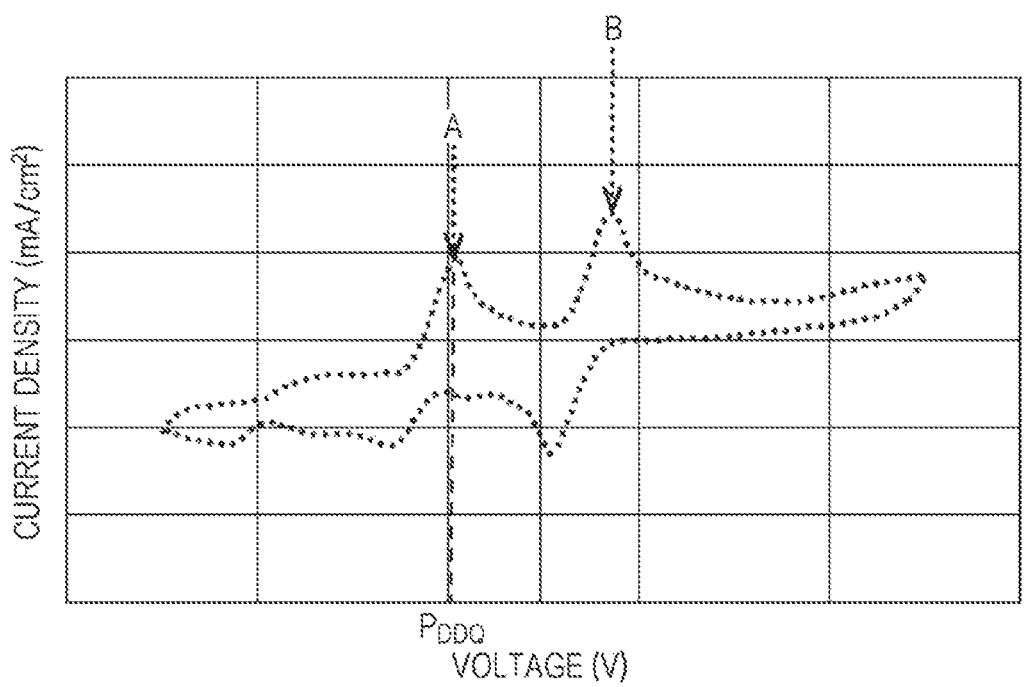
FIG. 18 is a graph showing an example of a current-voltage curve of CV measurement of an organic hydride solution when DDQ is used as a mediator.

FIG. 17 is a graph showing an example of a current-voltage curve of CV measurement of an organic hydride solution when chloranil was used as a mediator. FIG. 18 is a graph showing an example of a current-voltage curve of CV measurement of an organic hydride solution when DDQ was used as a mediator.

Both graphs of FIGS. 17 and 18 have peaks A and B showing oxidation of the mediators. Peak A corresponds to the oxidation of the mediator when the first hydrogen atom is desorbed from the hydroquinone body, and peak B corresponds to the oxidation of the mediator when the second hydrogen atom is desorbed from the hydroquinone body.

Accordingly, the oxidation peak voltage $P_{CN}$ corresponding to peak A of oxidation of chloranil and the oxidation peak voltage $P_{DDQ}$ corresponding to peak A of oxidation of DDQ were measured. These oxidation peak voltages were corrected with the voltage (1.188 V) of the reference electrode (Pt electrode), and the corrected values were compared to each other.

The results of measurement when trihexyltetradecylphosphonium bis(trifluoromethylsulfonyl)imide was used as the electrolyte were that the oxidation peak voltage $P_{CN}$ was −1.255 V and its corrected value was −0.067 V, whereas the oxidation peak voltage $P_{DDQ}$ was −1.025 V and its corrected value was 0.163 V.

In addition, when a trihexyltetradecylphosphonium bis(fluoroalkyl)phosphate was used as the electrolyte, the oxidation peak voltage $P_{CN}$ was −1.195 V and its corrected value was −0.007 V, whereas the oxidation peak voltage $P_{DDQ}$ was −1.015 V and its corrected value was 0.173 V.

As described above, the dehydrogenation apparatus 100 and the hydrogen desorption method of this example can perform dehydrogenation of an organic hydride by using chloranil as a mediator at a voltage lower than that when DDQ was used as a mediator. Accordingly, the dehydrogenation apparatus 100 and the hydrogen desorption method of the example can decrease the electric power necessary for dehydrogenation of an organic hydride, compared to the case using DDQ as a mediator.

In the explanation of the embodiment, a chloranil n-mer (n≥1) was used as the quinone being insensitive to water. Other quinones that are insensitive to water compared to DDQ may be used. For example, benzoquinone may be used.

In the embodiment, when the electrolyte is DDQ and the proton conductor is made of a material (Nafion) that is required to be humidified, the DDQ is inactivated and dehydrogenation does not proceed, but dehydrogenation is inferred to proceed by using a proton conductor that does not need to be humidified. Examples of the proton conductor not needing to be humidified include inorganic electrolyte films, such as films of yttrium-doped barium zirconate (BZY), a compound composed of iron and tantalum, or a compound mainly composed of stannous pyrophosphate; and inorganic-organic hybrid electrolyte films composed of porous inorganic materials and ionic liquids absorbed therein. In the embodiments described above, dehydrogenation of organic hydrides was shown as one example of various electrochemical reactions of organic hydrides, but the present disclosure is not limited thereto. For example, the liquid containing the alicyclic saturated hydrocarbon having a tertiary carbon atom bearing the saturated hydrocarbon side chain, the quinone, and the electrolyte may be applied to an electrode reaction of the anode of a fuel cell using the alicyclic saturated hydrocarbon as fuel.

The hydrogen desorption method and the dehydrogenation apparatus of the present disclosure are utilizable in various fields and are useful, in particular, as a method of extracting hydrogen stored in an alicyclic saturated hydrocarbon having a tertiary carbon atom bearing a saturated hydrocarbon side chain.

What is claimed is:

1. A hydrogen desorption method comprising:
   bringing a liquid containing an alicyclic saturated hydrocarbon having a tertiary carbon atom bearing a saturated hydrocarbon side chain, a quinone, and an electrolyte into contact with an anode; and
   desorbing hydrogen from the alicyclic saturated hydrocarbon wherein the hydrogen is desorbed from the alicyclic saturated hydrocarbon by applying a voltage between the anode and a cathode.

2. The hydrogen desorption method according to claim 1, wherein
   the liquid further contains a polar solvent.

3. The hydrogen desorption method according to claim 1, wherein
   the alicyclic saturated hydrocarbon is at least one of a monocyclic saturated hydrocarbon having a tertiary carbon atom bearing a saturated hydrocarbon and a polycyclic saturated hydrocarbon.

4. The hydrogen desorption method according to claim 1, wherein
   the monocyclic saturated hydrocarbon having a tertiary carbon atom bearing a saturated hydrocarbon side chain contains at least one selected from the group consisting of methylcyclohexane and di methylcyclohexane.

5. The hydrogen desorption method according to claim 1, wherein
   the quinone contains 2,3-dichloro-5,6-dicyano-p-benzoquinone.

6. The hydrogen desorption method according to claim 1, wherein
   the quinone contains chloranil.

7. The hydrogen desorption method according to claim 1, wherein
   the hydrogen is desorbed from the alicyclic saturated hydrocarbon by applying a direct voltage of 0.07 V or more to the anode with a single cell.

8. The hydrogen desorption method according to claim 1, wherein
   the hydrogen is desorbed from the alicyclic saturated hydrocarbon by applying a direct voltage of 1.5V or less between the anode and the cathode with a single cell.

9. The hydrogen desorption method according to claim 1, further comprising:
   conducting hydrogen desorbed on the anode to the cathode via a polymer electrolyte film.

10. The hydrogen desorption method according to claim 9, further comprising:
    supplying a cathode fluid to the cathode; and
    humidifying the cathode fluid.

\* \* \* \* \*